US012311009B2

(12) United States Patent
Puca

(10) Patent No.: US 12,311,009 B2
(45) Date of Patent: *May 27, 2025

(54) METHODS FOR TREATING HUNTINGTON'S DISEASE USING A POLYNUCLEOTIDE ENCODING A VTFT ISOFORM OF A BPIFB4 PROTEIN

(71) Applicant: LGV1 S.R.L, Naples (IT)

(72) Inventor: Annibale Alessandro Puca, Naples (IT)

(73) Assignee: LGV1 S.R.L., Naples (IT)

(*) Notice: Subject to any disclaimer, the term of this patent is extended or adjusted under 35 U.S.C. 154(b) by 859 days.

This patent is subject to a terminal disclaimer.

(21) Appl. No.: 16/639,185

(22) PCT Filed: Aug. 16, 2018

(86) PCT No.: PCT/EP2018/072184
§ 371 (c)(1),
(2) Date: Feb. 14, 2020

(87) PCT Pub. No.: WO2019/034723
PCT Pub. Date: Feb. 21, 2019

(65) Prior Publication Data
US 2021/0128681 A1 May 6, 2021

(30) Foreign Application Priority Data
Aug. 16, 2017 (EP) .................... 17186528

(51) Int. Cl.
| | |
|---|---|
| *A61K 38/00* | (2006.01) |
| *A61K 38/17* | (2006.01) |
| *A61K 48/00* | (2006.01) |
| *A61P 25/00* | (2006.01) |
| *A61P 25/14* | (2006.01) |
| *A61P 25/16* | (2006.01) |
| *A61P 25/28* | (2006.01) |
| *C07K 14/00* | (2006.01) |
| *C07K 14/47* | (2006.01) |
| *C12N 15/63* | (2006.01) |
| *A61K 38/16* | (2006.01) |
| *C07K 14/435* | (2006.01) |

(52) U.S. Cl.
CPC ...... *A61K 38/1709* (2013.01); *A61K 38/1751* (2013.01); *A61P 25/00* (2018.01); *A61P 25/14* (2018.01); *A61P 25/16* (2018.01); *A61P 25/28* (2018.01); *A61K 38/16* (2013.01); *A61K 38/17* (2013.01); *A61K 48/00* (2013.01); *C07K 14/00* (2013.01); *C07K 14/435* (2013.01); *C07K 14/47* (2013.01)

(58) Field of Classification Search
CPC .... A61K 38/1709; A61K 38/00; A61K 38/17; C07K 14/4702; C07K 14/4742; C07K 14/47
See application file for complete search history.

(56) References Cited

U.S. PATENT DOCUMENTS

| | | | | |
|---|---|---|---|---|
| 11,208,447 B2* | 12/2021 | Puca | ................. | A61P 29/00 |
| 11,891,421 B2* | 2/2024 | Puca | ................. | A61P 27/12 |
| 2004/0092715 A1* | 5/2004 | Ding | ................. | C12Q 1/6883 |
| | | | | 435/325 |
| 2015/0344536 A1* | 12/2015 | Puca | ................. | A61P 27/06 |
| | | | | 435/325 |

FOREIGN PATENT DOCUMENTS

| | | | | |
|---|---|---|---|---|
| EP | 2749569 A1 | 7/2014 | | |
| EP | 17186528.0 | * 8/2017 | ............ | C07K 14/47 |
| NO | 200179269 A2 | 10/2001 | | |
| WO | 2002063008 A3 | 8/2002 | | |
| WO | 2010071832 A1 | 6/2010 | | |
| WO | 2014102343 A1 | 7/2014 | | |

OTHER PUBLICATIONS

Soto et al., Arch Neurol. 2008; 65: 184-189.*
Abramov et al., Biochem. Soc. Transac. 2017; 45:1025-1033.*
Hashimoto et al., NeuroMol. Med. 2003; 4: 21-35.*
Falkenburger et al., J. Neural. Transm, 2006; 70:261-268.*
Tayebati, Mech. Ageing Dev. 2006. 127: 100-8.*
Sarter, Neurosci. and Biobehav. Rev. 2004. 28: 645-650.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Anger. Neurotoxicology 1991. 12: 403-13.*
Jagmag et al., Front. Neurosci. 2016; 9:503. Doi:10.3389/fnins.2015.00503.*
Potashikin et al., Parkinson's Disease, 2011; 658083; doi: 104061/2011/658083.*
Henstridge et al., Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Johri et al., J. Pharmacol. Exp. Thera. 2012; 342:619-630.*
Van Bergen et al., Eye and Brain, 2011; 3:29-47.*
Beletkaia E., et al., Biochimica et Biophysica Acta 1863 (2016) 607-616.
Bingle et al., Biochem Soc Trans., 2011, 39(4) pp. 977-983.

(Continued)

*Primary Examiner* — Chang-Yu Wang
(74) *Attorney, Agent, or Firm* — Hoffmann & Baron LLP

(57) ABSTRACT

The invention relates inter alia to a protein which is a VTFT isoform of a BPIFB4 protein or a functional fragment thereof for use in the treatment or prophylaxis of a condition selected from neuronal diseases and injuries, said diseases and injuries being associated with mitochondrial dysfunction and/or protein aggregation and/or ameliorated by CXCR4 activation.

8 Claims, 17 Drawing Sheets
Specification includes a Sequence Listing.

(56) References Cited

OTHER PUBLICATIONS

Boldogh I.R., Pon. L.A. Biochim Biophys Acta. (2006) 1763(5-6):450-62.
Bubber, P. et al., Ann. Neurol. 57 (2005) 695-703.
Cagalinec M. et al., PLoSBiol. Jul. 19, 2016;14(7).
Chen, C.M, et al., Biochem. Biophys. Res. Commun. 359 (2007) 335-340.
Clarkson, et al., Adv. Exp. Med. Biol (2012), 946, 309-333.
Delgado-Martin, C., et al, J. Biol. Chem. (2011), 286:43, 37222-37236.
Devi, L., et al., J. Biol. Chem. 283 (2008) 9089-9100.
Ferro, A., et al., Journal of Visualized Experiments, (2017) Issue 119, 22.
Fink, A.J., Folding & Design Feb. 1998, 3:R9-R23.
Gao et al, J. Virol, (2004) 78: 6381-6388.
Grenier, C. et al., J Neurochem. Jun. 2006;97(5):1456-66.
Jaiswal, M.K. and Keller, B.U., Mol. Pharmacol. 75 (2009) 478-489.
Kabashima K., et al., Biochem. Biophys. Res. Commun. (2007), 361:4, 1012-1016.
Kinane et al., Periodontology, 2007, 45 pp. 14-34.
Koeppen, A.H. Cerebellum (2005) 4: 62.
Lim, D., et al., J. Biol. Chem. 283 (2008) 5780-5789.
Liu, J-M., et al., Scientific Reports 7, (2017) Article No. 64.
Manczek, M. et al., Hum. Mol. Genet. 15 (2006) 1437-1449.
Moreira, et al., J. Alzheimers Dis. 16 (2009) 741-761.
Mori et al., Virology, (2004) 330(2): 375-383.
Orr, A.L., et al., J. Neurosci. 28 (2008) 2783-2792.
Pagano and Costello, Adv Exp Med Biol. (2012) 724:291-9.
Santos, R., et al., Antioxidants & Redox Signaling. (2010) 13(5):651-690.
Scaglia F, Northrop JL. CNS Drugs. (2006);20(6):443-64.
Schmidt S.V., et al., Front. Immunol. (2012); 4:3, 274.
Takeuchi, H., et al., Neurosci Lett (2007) 426, 69-74 .
Tysseling, V. M., et al., J Neuroinflammation (2011) 8, 16.
Valla, J, et al., Mitochondrion 6 (2006) 323-330.
Zaccagnino et al., Int. J.Biochem. Cell Biol. (2012), 44:11, 1962-1969.

* cited by examiner

A hBPIFB4

SEQUENCE LISTING

```
<160> NUMBER OF SEQ ID NOS: 2

<210> SEQ ID NO 1
<211> LENGTH: 575
<212> TYPE: PRT
<213> ORGANISM: Homo sapiens

<400> SEQUENCE: 1

Met Leu Gln Gln Ser Asp Ala Leu His Ser Ala Leu Arg Glu Val Pro
1               5                   10                  15

Leu Gly Val Gly Asp Ile Pro Tyr Asn Asp Phe His Val Arg Gly Pro
            20                  25                  30
```

```
Pro Pro Val Tyr Thr Asn Gly Lys Lys Leu Asp Gly Ile Tyr Gln Tyr
            35                  40                  45

Gly His Ile Glu Thr Asn Asp Asn Thr Ala Gln Leu Gly Gly Lys Tyr
50                  55                  60

Arg Tyr Gly Glu Ile Leu Glu Ser Gly Ser Ile Arg Asp Leu Arg
65                  70                  75                  80

Asn Ser Gly Tyr Arg Ser Ala Glu Asn Ala Tyr Gly Gly His Arg Gly
                85                  90                  95

Leu Gly Arg Tyr Arg Ala Ala Pro Val Gly Arg Leu His Arg Arg Glu
                100                 105                 110

Leu Gln Pro Gly Glu Ile Pro Pro Gly Val Ala Thr Gly Ala Val Gly
            115                 120                 125

Pro Gly Gly Leu Leu Gly Thr Gly Gly Met Leu Ala Ala Asp Gly Ile
130                 135                 140

Leu Ala Gly Gln Gly Gly Leu Leu Gly Gly Gly Leu Leu Gly Asp
145                 150                 155                 160

Gly Gly Leu Leu Gly Gly Gly Val Leu Gly Val Leu Gly Glu Gly
                165                 170                 175

Gly Ile Leu Ser Thr Val Gln Gly Ile Thr Gly Leu Arg Ile Val Glu
            180                 185                 190

Leu Thr Leu Pro Arg Val Ser Val Arg Leu Leu Pro Gly Val Gly Val
            195                 200                 205

Tyr Leu Ser Leu Tyr Thr Arg Val Ala Ile Asn Gly Lys Ser Leu Ile
            210                 215                 220

Gly Phe Leu Asp Val Ala Val Glu Val Asn Ile Thr Ala Lys Val Arg
225                 230                 235                 240

Leu Thr Met Asp Arg Thr Gly Tyr Pro Arg Leu Val Ile Glu Arg Cys
                245                 250                 255

Asp Thr Leu Leu Gly Gly Ile Lys Val Lys Leu Leu Arg Gly Leu Leu
            260                 265                 270

Pro Asn Leu Val Asp Asn Leu Val Thr Arg Val Leu Ala Asp Val Leu
            275                 280                 285

Pro Asp Leu Leu Cys Pro Ile Val Asp Val Leu Gly Leu Val Asn
            290                 295                 300

Asp Gln Leu Gly Leu Val Asp Ser Leu Ile Pro Leu Gly Ile Leu Gly
305                 310                 315                 320

Ser Val Gln Tyr Thr Phe Ser Ser Leu Pro Leu Val Thr Gly Glu Phe
                325                 330                 335

Leu Glu Leu Asp Leu Asn Thr Leu Val Gly Glu Ala Gly Gly Gly Leu
                340                 345                 350

Ile Asp Tyr Pro Leu Gly Trp Pro Ala Val Ser Pro Lys Pro Met Pro
                355                 360                 365

Glu Leu Pro Pro Met Gly Asp Asn Thr Lys Ser Gln Leu Ala Met Ser
    370                 375                 380

Ala Asn Phe Leu Gly Ser Val Leu Thr Leu Leu Gln Lys Gln His Ala
385                 390                 395                 400

Leu Asp Leu Asp Ile Thr Asn Gly Met Phe Glu Glu Leu Pro Pro Leu
                405                 410                 415

Thr Thr Ala Thr Leu Gly Ala Leu Ile Pro Lys Val Phe Gln Gln Tyr
            420                 425                 430

Pro Glu Ser Cys Pro Leu Ile Ile Arg Ile Gln Val Leu Asn Pro Pro
            435                 440                 445
```

```
Ser Val Met Leu Gln Lys Asp Lys Ala Leu Val Lys Val Leu Ala Thr
450                 455                 460
Ala Glu Val Met Val Ser Gln Pro Lys Asp Leu Glu Thr Thr Ile Cys
465                 470                 475                 480
Leu Ile Asp Val Asp Thr Glu Phe Leu Ala Ser Phe Ser Thr Glu Gly
                485                 490                 495
Asp Lys Leu Met Ile Asp Ala Lys Leu Glu Lys Thr Ser Leu Asn Leu
                500                 505                 510
Arg Thr Ser Asn Val Gly Asn Phe Asp Ile Gly Leu Met Glu Val Leu
                515                 520                 525
Val Glu Lys Ile Phe Asp Leu Ala Phe Met Pro Ala Met Asn Ala Val
530                 535                 540
Leu Gly Ser Gly Val Pro Leu Pro Lys Ile Leu Asn Ile Asp Phe Ser
545                 550                 555                 560
Asn Ala Asp Ile Asp Val Leu Glu Asp Leu Leu Val Leu Ser Ala
                565                 570                 575
```

<210> SEQ ID NO 2
<211> LENGTH: 1728
<212> TYPE: DNA
<213> ORGANISM: Homo sapiens

<400> SEQUENCE: 2

| | | | | | |
|---|---|---|---|---|---|
| atgctgcagc | aaagtgatgc | tctccactcg | gccctgagag | aggtgccctt | gggtgttggt | 60 |
| gatattccct | acaatgactt | ccatgtccga | ggaccccccc | cagtatatac | caacggcaaa | 120 |
| aaacttgatg | gtatttacca | gtatggtcac | attgagacca | cgacaacac | tgctcagctg | 180 |
| gggggcaaat | accgatatgg | tgagatcctt | gagtccgagg | aagcatcag | ggacctccga | 240 |
| aacagtggct | atcgcagtgc | cgagaatgca | tatggaggcc | acaggggcct | cgggcgatac | 300 |
| agggcagcac | ctgtgggcag | gcttcaccgg | cgagagctgc | agcctggaga | aatcccacct | 360 |
| ggagttgcca | ctgggcggt | gggcccaggt | ggtttgctgg | cactggagg | catgctggca | 420 |
| gctgatggca | tcctcgcagg | ccaaggtggc | ctgctcggcg | gaggtggtct | ccttggtgat | 480 |
| ggaggacttc | ttggaggagg | gggtgtcctg | gcgtgctcg | gcgagggtgg | catcctcagc | 540 |
| actgtgcaag | gcatcacggg | gctgcgtatc | gtggagctga | ccctccctcg | ggtgtccgtg | 600 |
| cggctcctgc | ccgcgtggg | tgtctacctg | agcttgtaca | cccgtgtggc | catcaacggg | 660 |
| aagagtctta | ttggcttcct | ggacgtcgca | gtagaagtga | acatcacagc | caaggtccgg | 720 |
| ctgaccatgg | accgcacggg | ttatcctcgg | ctggtcattg | agcgatgtga | caccctccta | 780 |
| gggggcatca | aagtcaagct | gctgcgaggg | cttctcccca | atctcgtgga | caatttagtg | 840 |
| acccgagtcc | tggccgacgt | cctccctgac | ttgctctgcc | ccatcgtgga | tgtggtgctg | 900 |
| ggtcttgtca | tgaccagct | gggcctcgtg | gattctctga | ttcctctggg | gatattggga | 960 |
| agtgtccagt | acaccttctc | cagcctcccg | cttgtgaccg | gggaattcct | ggagctggac | 1020 |
| ctcaacacgc | tggttgggga | ggctggagga | ggactcatcg | actacccatt | ggggtggcca | 1080 |
| gctgtgtctc | ccaagccgat | gccagagctg | cctcccatgg | gtgacaacac | caagtcccag | 1140 |
| ctggccatgt | ctgccaactt | cctgggctca | gtgctgactc | tactgcagaa | gcagcatgct | 1200 |
| ctagacctgg | atatcaccaa | tggcatgttt | gaagagcttc | ctccacttac | cacagccaca | 1260 |
| ctggagcccc | tgatcccaa | ggtgttccag | cagtacccg | agtcctgccc | acttatcatc | 1320 |
| aggatccagt | gctgaaccc | accatctgtg | atgctgcaga | aggacaaagc | gctggtgaag | 1380 |
| gtgttggcca | ctgccgaggt | catggtctcc | cagcccaaag | acctggagac | taccatctgc | 1440 |

```
ctcattgacg tggacacaga attcttggcc tcattttcca cagaaggaga taagctcatg   1500
attgatgcca agctggagaa gaccagcctc aacctcagaa cctcaaacgt gggcaacttt   1560
gatattggcc tcatggaggt gctggtggag aagatttttg acctggcatt catgcccgca   1620
atgaacgctg tgctgggttc tggcgtccct ctccccaaaa tcctcaacat cgactttagc   1680
aatgcagaca ttgacgtgtt ggaggacctt ttggtgctga gcgcatga                1728
```

METHODS FOR TREATING HUNTINGTON'S DISEASE USING A POLYNUCLEOTIDE ENCODING A VTFT ISOFORM OF A BPIFB4 PROTEIN

CROSS REFERENCE TO RELATED APPLICATIONS

The present application is a National Stage Application claiming priority from PCT Application No. PCT/EP2018/072184 filed Aug. 16, 2018, which in turn claims priority from EP Application Serial No. 17186528.0 filed Aug. 16, 2017. Applicant claims the benefits of 35 U.S.C. § 120 as to the said PCT application, and priority under 35 U.S.C. § 119 as to the said EP application, and the entire disclosures of all applications are incorporated herein by reference in their entireties.

FIELD OF THE INVENTION

The present invention relates to novel therapeutic uses of the VTFT isoform of the Bactericidal/Permeability Increasing protein family B, member 4 (BPIFB4) protein, in particular for the treatment or prophylaxis of conditions selected from neuronal diseases and injuries, said diseases and injuries being associated with mitochondrial dysfunction and/or protein aggregation and/or ameliorated by CXCR4 activation.

BACKGROUND OF THE INVENTION

The inventors previously reported a longevity-associated variant of the BPIFB4 protein, a multitasking protein involved in processes that are important for cellular and organism homeostasis and whose role in modulating eNOS is potentiated by the VTFT isoform, a genetic variant found to be associated with exceptional longevity as compared with the predominant INLI isoform ("wild type") and the rare INFT isoform. See Villa et al., (2015) and WO2014102343 the content of which is incorporated herein by reference in its entirety.

WO2014102343 teaches that the VTFT isoform of BPIFB4 has a range of therapeutic uses. Villa et al., (2015) shows that the protein can be widely distributed around the body, including for example in the brain, femoral bone marrow, adipose tissue and the liver following intra-arterial administration of a gene therapy vector.

Mitochondria are present in the cytoplasm of all eukaryotic cells of animals and higher plants. They are highly dynamic organelles which fulfil a plethora of functions critical for essential cellular functions including oxidative phosphorylation, energy production, intermediary metabolism, calcium buffering, reactive oxygen species generation and detoxification, and the regulation of apoptosis.

The brain is a highly metabolic tissue: it receives 15% of cardiac output and accounts for 20% of total body oxygen consumption. This energy requirement is largely driven by neuronal demand for energy to maintain ion gradients across the plasma membrane that are critical for the generation of action potentials. This intense energy requirement is continuous; even brief periods of oxygen or glucose deprivation result in neuronal death.

Mitochondria are essential for neuronal function because the limited glycolytic capacity of neurons makes them highly dependent on aerobic oxidative phosphorylation (OXPHOS) for their energetic needs (P. G. Sullivan, et al., (2009)). However, OXPHOS is a major source of toxic endogenous free radicals, including hydrogen peroxide ($H_2O_2$), hydroxyl ($\cdot OH$) and superoxide ($O_2{\cdot}^-$) radicals that are products of normal cellular respiration.

It is well recognized that reactive oxygen species (ROS) and reactive nitrogen species (RNS) can be either harmful or beneficial to living systems. Beneficial effects of reactive species occur at low/moderate concentrations and involve physiological roles in cellular responses to noxia. Oxidative stress occurs if the amount of free radical species produced overwhelms the cells' capacity to neutralize them, which is followed by mitochondrial dysfunction and cellular damage.

Reactive species generated by mitochondria have several cellular targets, including mitochondrial components themselves (lipids, proteins and DNA). The lack of histones in mitochondrial DNA (mtDNA) and the diminished capacity for DNA repair render mitochondria a vulnerable target of oxidative stress events.

Many lines of evidence suggest that mitochondria have a central role in aging-related neuronal diseases and injuries.

C-X-C chemokine receptor type 4 (CXCR4), is a G-coupled receptor for the ligand stromal-derived-factor-1 (SDF-1, also called CXCL12). The activation of CXCR4 by its chemokine ligand regulates a variety of functions in the central nervous system, including the migration and differentiation of endogenous neural stem cells (Takeuchi, H., et al., (2007)). Although the intracellular expression level of CXCR4 was very low in normal tissues, it is significantly increased in injured neurons. CXCR4 inhibition through AMD3100 reduces the injury repair process by targeting β-catenin signalling pathway (J-M. Liu. et al., (2017)).

CXCR4 modulates cytoskeleton and mitochondrial activity, which are tightly interconnected as they both influence each other as well as protein aggregation (Boldogh. I. R., Pon. L. A. (2006)). It is now clear that a lack of protein homeostasis is a key common denominator of many diseases (A. L. Fink, (1998)). Protein homeostasis depends mostly on the energy availability to support high energy demanding processes such as translation, protein folding and protein stability, which is highly correlated with protein aggregation. Impairment of mitochondrial function also results in excess protein aggregation and therefore cellular damage. Thus, it is also believed that mitochondria have a vital role in maintaining cell health and mitigating pathologies by controlling (or possibly eliminating) built up of misfolded or aggregated proteins.

Alzheimer's disease (AD) is the most common cause of dementia among older people. Accumulating evidence indicates that mitochondrial abnormalities and oxidative damage are early events in AD. In addition to evidence gathered in animal models of the disease, see for instance M. Manczak, et al., (2006), that oxidative stress is an early event in AD pathophysiology, observations in postmortem AD brain and fibroblasts points to evidence of impaired activity of three tricarboxylic acid cycle (TCA) complexes, pyruvate dehydrogenase, isocitrate dehydrogenase and α-ketoglutarate dehydrogenase (P. Bubber, et al., (2005)). Similarly, reduced respiratory chain activities in complexes I, III and IV have been found in platelets and lymphocytes from AD patients and postmortem brain tissue (J. Valla, et al., (2006)).

Parkinson's disease (PD) is characterized by degeneration and death of dopaminergic neurons in the pars compacta of the substantia nigra and by the presence of Lewy bodies. Dopaminergic neurons in the substantia nigra operate in a pathway that controls voluntary movement: their death results in the inability to coordinate movement. It is well established that oxidative stress and mitochondrial dysfunction are associated with the degeneration of dopaminergic neurons in PD.

Accumulating evidence indicates that PD-associated genes directly or indirectly impinge on mitochondrial integrity, thereby providing a link to pathophysiological alterations observed in sporadic PD. Mitochondria were demonstrated to be one of the direct targets of α-synuclein during the pathogenesis of PD (L. Devi, et al., (2008)). α-Synuclein accumulates in the mitochondria of the striatum and substantia nigra of PD patients impairing mitochondrial complex I activity and causing oxidative stress. Moreover, the neurotoxin 1-methyl-4-phenylpyridium (MPP+), which is commonly used to induce parkinsonism in animal models, inhibits mitochondrial complex I resulting in the generation of free radicals. Mitochondrial alterations lead to an imbalance in cellular oxidative status inducing proteasomal deregulation. This may exacerbate protein aggregation and consequently engender degenerative events.

Huntington's disease (HD) is an autosomal-dominant disease caused by an abnormal expanded polyglutamine repeat in the Huntington (Htt) protein, which leads to the degeneration of the neurons in the striatum and cortex. A number of studies indicate that mitochondrial dysfunction is central to the pathogenesis of HD. Reduction of the activities of complexes II, III and IV has been observed in the caudate and putamen of HD patients and increased glucose utilization relative to oxygen utilization in the striatum of early HD patients. Chen and collaborators (C. M. Chen, et al., (2007)) also observed mitochondrial abnormalities and oxidative damage in the peripheral blood of HD patients. Moreover, Lim and co-workers (D. Lim, et al., (2008)) reported that mutant Htt expression induced PTP opening and disruption of mitochondrial $Ca^{2+}$ homeostasis. Similar results were obtained in mitochondria isolated from cells expressing mutant Htt, suggesting that mitochondrial dysfunction plays a central role in HD pathogenesis.

Recently, it was suggested that mtDNA damage is an early biomarker for HD-associated neurodegeneration supporting the hypothesis that mtDNA lesions might contribute to the pathogenesis observed in HD. Orr and colleagues (A. L. Orr, et al., (2008)) reported that specific N-terminal mutant Htt fragments, before they form aggregates, would impair mitochondrial function directly.

ALS is the most common adult-onset motor neuron disease resulting in weakness, paralysis and subsequent death. 90% of cases are sporadic, and 10% of cases are familial. In 20% of the familial cases of ALS, motor neuron loss is related to mutations of the Cu/Zn superoxide dismutase (SOD1) gene. Mutant SOD1 has been shown to exert deleterious effects through a gain of function rather than a loss of activity. Additionally, the presence of mutant SOD1 within motor neurons causes alterations of the mitochondrial respiratory chain, specifically in mitochondrial complexes II and IV. A recent study also shows that SOD1 increases the vulnerability of mitochondria and perturbs $Ca^{2+}$ homeostasis in SOD1G93A mice, a mouse model of ALS (M. K. Jaiswal, B. U. Keller, (2009)). Further, it was reported that mitochondrial dysfunction in SOD1G93A bearing astrocytes promotes motor neuron degeneration, this effect being prevented by mitochondrial-targeted antioxidants.

There is evidence of abnormal structure and number of mitochondria and compromised mitochondrial function in ALS motor neurons and skeletal muscle. This is corroborated by findings of altered respiratory chain enzyme activities and CNS energy hypometabolism in the spinal cord and motor cortex of ALS patients.

Spino-cerebellar ataxia (SCA) is one of a group of genetic disorders characterized by slow and progressive loss of gait coordination often associated with poor coordination of hands, speech, and eye movements. Frequently, atrophy of the cerebellum occurs.

The SCA-1, SCA-2, SCA-3/Machado-Joseph disease (MJD), SCA-6, SCA-7, and SCA-17 are classified as "polyglutamine diseases" caused by pathological cytosine-adenine-guanine (CAG) trinucleotide repeat expansions in the coding region of the mutated genes: the translated proteins contain abnormally long polyglutamine stretches. Despite their clinical and genetic heterogeneity, the ataxia-causing lesions in the brain invariably affect the "cerebellar module" that is defined as a reciprocal circuitry between the cerebellar cortex, the dentate nuclei, and the inferior olivary nuclei. Whilst the specific role of polyglutamine-containing intranuclear and cytoplasmic inclusion bodies is under investigation, protein aggregation may be the common step in the pathogenesis of these otherwise rather heterogeneous disorders (Koeppen, A. H. (2005)).

Spinocerebellar ataxia type 1 (SCA1), due to an unstable polyglutamine expansion within the ubiquitously expressed Ataxin-1 protein, leads to the premature degeneration of Purkinje cells (PCs), decreasing motor coordination and death within 10-15 years of diagnosis. Currently, there are no therapies available to slow down disease progression. Proteomic profiling of Sca1154Q/2Q mice at a symptomatic stage revealed prominent alterations in mitochondrial proteins and age-dependent alterations in mitochondrial morphology was observed, with impairment of the electron transport chain complexes (ETC) and decrease in ATPase activity. Surprisingly, mitochondria-targeted antioxidant MitoQ treatment both presymptomatically and when symptoms were evident ameliorated mitochondrial morphology and restored the activities of the ETC complexes in Sca1154Q/2Q mice. Notably, MitoQ slowed down the appearance of SCA1-linked neuropathology such as lack of motor coordination as well as prevented oxidative stress-induced DNA damage (Ferro A., et al., (2017)).

Friedreich Ataxia (FA) is a slow, progressive disorder of the nervous system and muscles, which results in an inability to co-ordinate voluntary muscle movements (ataxia). This condition is caused by the degeneration of nerve tissue in the spinal cord and of nerves that extend to peripheral areas such as the arms and legs. In FA, there is a defect in a gene on chromosome 9. The corresponding protein that is altered due to this defect is called frataxin and is produced in diminished amounts. Frataxin is found in mitochondria. When frataxin levels are low, cells (particularly in the brain, spinal cord, and muscle cells) cannot produce energy properly and the build-up of toxic by-products leads to "oxidative stress", which has the potential to destroy cells (Santos R., et al., (2010), https://www.mda.org/disease/friedreichs-ataxia/causes-inheritance, accessed 14 Aug. 2017).

Down syndrome (DS) is characterized by low muscle tone, small stature, an upward slant to the eyes, and a single deep crease across the center of the palm. DS-associated neurodegeneration recalls the clinical course of Alzheimer disease (AD), due to DS progression toward dementia and amyloid plaques reminiscent of AD clinical course. Ultrastructural and biochemical abnormalities were reported in mitochondria from human DS patients and from trisomy 16 (Ts16) mice. Together, in vivo alterations of mitochondrial function are consistent with a prooxidant state as a phenotypic hallmark in DS (Pagano, Castello, (2012)).

Wolfram syndrome (WS) is a genetic disorder. Brain abnormalities occur at the earliest stage of clinical symptoms, suggesting that Wolfram syndrome has a pronounced impact on early brain development. The clinical symptoms of WS resemble mitochondrial disease symptoms, suggesting strong mitochondrial involvement (Cagalinec M. et al., (2016)). Deficiency of the gene WFS1 triggers an ER-stress cascade, which impairs the function of the IP3-receptor calcium channel, leading to altered calcium homeostasis. The latter leads to dysregulation of mitochondrial dynamics, as characterized by augmented mitophagy—a selective degradation of mitochondria—and inhibited mitochondrial trafficking and fusion, which results in lower levels of ATP and, thus, inhibits neuronal development.

The mitochondrial myopathy encephalopathy, lactic acidosis with stroke-like episodes (MELAS) syndrome is one of the most frequently occurring, maternally inherited mitochondrial disorders. This syndrome is associated with a number of point mutations in the mitochondrial DNA, with over 80% of the mutations occurring in the dihydrouridine loop of the mitochondrial transfer RNA(Leu(UUR)) [tRNA (Leu)((UUR))] gene. The pathophysiology of the disease is not completely understood; however, several different mechanisms are proposed to contribute to this disease. These include decreased aminoacylation of mitochondrial tRNA, resulting in decreased mitochondrial protein synthesis; changes in calcium homeostasis; and alterations in nitric oxide metabolism (Scaglia F, Northrop J L. (2006)).

Charcot-Marie-Tooth disease (CMT) comprises a group of disorders that affect peripheral nerves. CMT2A, the most common axonal form of CMT, is caused by mutations in Mitofusin 2, a protein associated with mitochondrial fusion. There is no cure for CMT, but physical therapy, occupational therapy, braces and other orthopedic devices, and even orthopedic surgery can help individuals cope with the disabling symptoms of the disease.

Creutzfeldt-Jakob disease (CJD) or prion disease is a rapidly progressive fatal neurodegenerative disorder caused by an abnormal isoform of a cellular glycoprotein known as the prion protein. In most CJD patients, the presence of 14-3-3 protein in the cerebrospinal fluid and/or a typical electroencephalogram (EEG) pattern, both of which are believed to be diagnostic for CJD, have been reported. However, a confirmatory diagnosis of CJD requires neuropathologic and/or immunodiagnostic testing of brain tissue obtained either at biopsy or autopsy. Cytoskeleton and mitochondria are dysfunctional in prion disease (Grenier. C. et al., (2006)). Indeed, transfection of prion protein in living cells generated aggresomes, and induced a major rearrangement of intermediate filament and mitochondrial networks.

Spinal cord injury (SCI) affects the nervous, vascular and immune systems. SCI can cause patients' sensory, motor and autonomic nerve dysfunction. The treatment for SCI can only ameliorate some secondary aspects, while the neurologic function of patients cannot be restored due to injured spinal cord cells. The intracellular expression level of CXCR4 is significantly increased in the injured neurons compared to healthy neurons. Although studies have found that the proliferation, migration and differentiation of endogenous neural stem cells were detected in the injured spinal cord, this process is limited and only a small number of stem cells can differentiate into neuron cells with neurologic function. Therefore, the promotion of the regeneration of nerve cells after SCI via CXCR4 activation is important for patients (Tysseling, V. M., et al., (2011)).

A variety of neuronal diseases involves protein aggregation, for example AD, trinucleotide repeat expansion diseases such as HD, SCA, FA, prion diseases (A. L. Fink, (1998)). Thus, a possible therapeutic strategy is aimed at improving mitochondrial function and a reduction of protein aggregation.

Ongoing therapeutic strategies for diseases characterized by mitochondrial dysfunction focus mainly on counteracting overproduction of ROS by mitochondria, a major cause of damage associated with mitochondrial dysfunction. Metabolic antioxidants involved in cellular energy production and acting as cofactors of several metabolic enzymes include creatine, α-lipoic acid, N-acetyl-carnitine and coenzyme Q10. However, metabolic antioxidants have showed disappointing results in clinical trials.

A major limitation to antioxidant therapy in treating neuronal diseases and injuries and other diseases characterized by mitochondrial dysfunction has been the inability to enhance the antioxidant levels within mitochondria. There is therefore a need for new therapies which prevent progression of the disorders and improve the quality of life of the patients.

Surprisingly, the present inventors have found that VTFT-BPIFB4 acts at multiple levels not hitherto described on pathways involved in neuronal diseases and injuries. The inventors have discovered that VTFT-BPIFB4 has activity as an enhancer of mitochondrial function, and as a reducer of protein aggregation in pathological conditions. The inventors have also discovered that the therapeutic effects of VTFT-BPIFB4 are mediated via CXCR4 and VTFT-BPIFB4 is believed to be an activator of CXCR4. The protein or protein encoding vector appears to be active in vivo following oral or parenteral administration.

SUMMARY OF THE INVENTION

Accordingly, the invention provides a protein which is a VTFT isoform of a BPIFB4 protein or a functional fragment thereof, a polynucleotide encoding said protein or fragment thereof and vector for use in the treatment or prophylaxis of a condition selected from neuronal diseases and injuries, said diseases and injuries being associated with mitochondrial dysfunction and/or protein aggregation and/or ameliorated by CXCR4 activation.

1A Oxygen consumption rate (OCR) profiling of HEK293 cells transfected with empty AAV vector ("EV") or vector carrying VTFT-hBPIFB4 DNA ("VTFT-hBPIFB4").

1B Graph shows the basal rate of oxygen consumption for cells transfected with empty AAV vector or vector carrying VTFT-hBPIFB4 DNA.

1C Graph shows the ATP-linked rate of oxygen consumption, which is the basal rate minus the rate measured after the addition of ATP-blocker oligomycin, for cells transfected with empty AAV vector or vector carrying VTFT-hBPIFB4 DNA.

Figure 2:
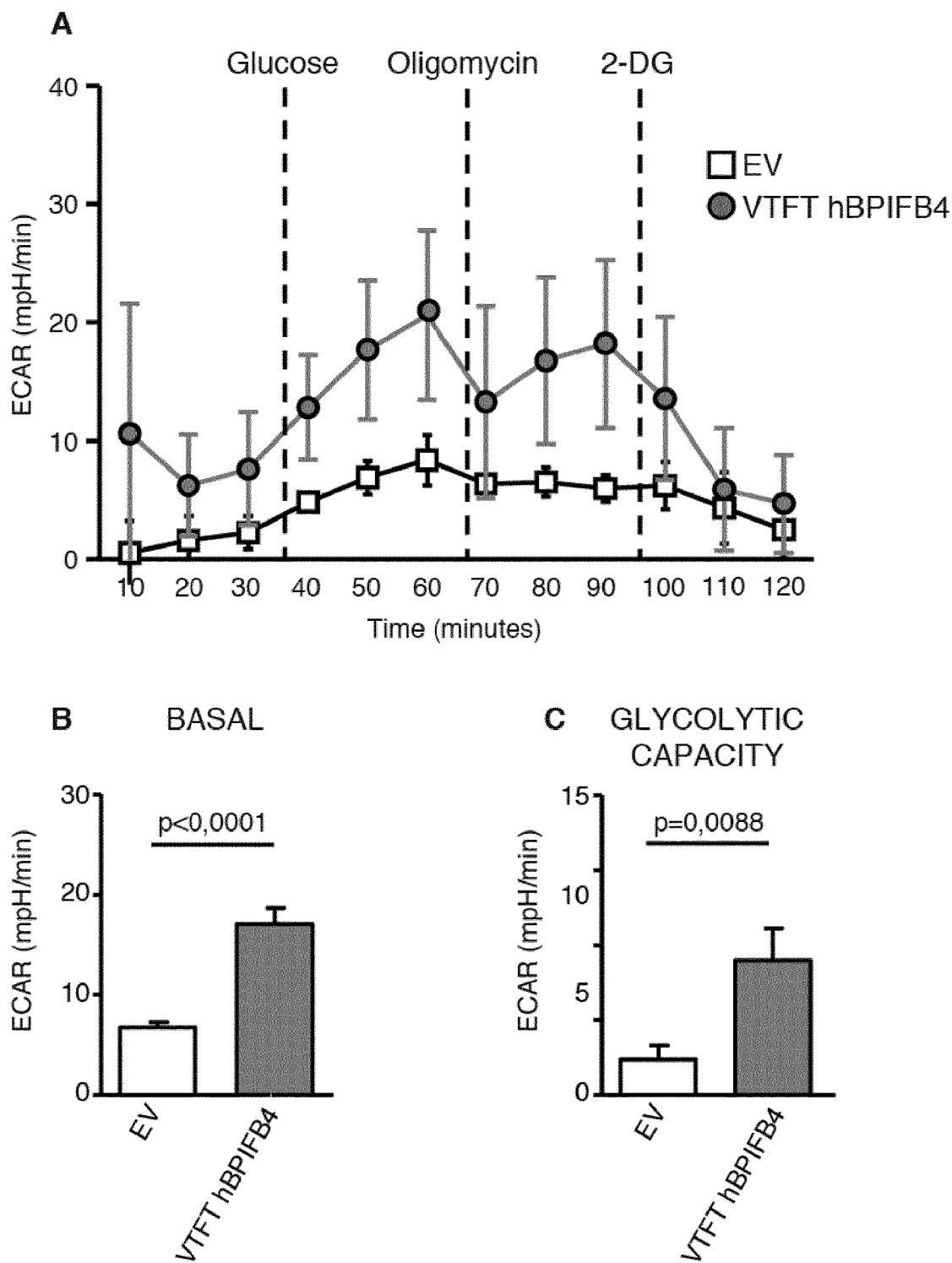

FIG. 2. Extracellular acidification rates analyses

2A Extracellular acidification rates (ECAR) profiling of HEK293 cells transfected with empty AAV vector ("EV") or vector carrying VTFT-hBPIFB4 DNA ("VTFT-hBPIFB4").

2B Graph shows the basal rate of ECAR for cells transfected with empty AAV vector or vector carrying VTFT-hBPIFB4 DNA.

2C Graph shows the glycolytic cell capacity, evaluated as the difference between maximal glycolysis and the treatment with glycolytic inhibitor 2DG, for cells transfected with empty AAV vector or vector carrying VTFT-hBPIFB4 DNA.

Figure 3:
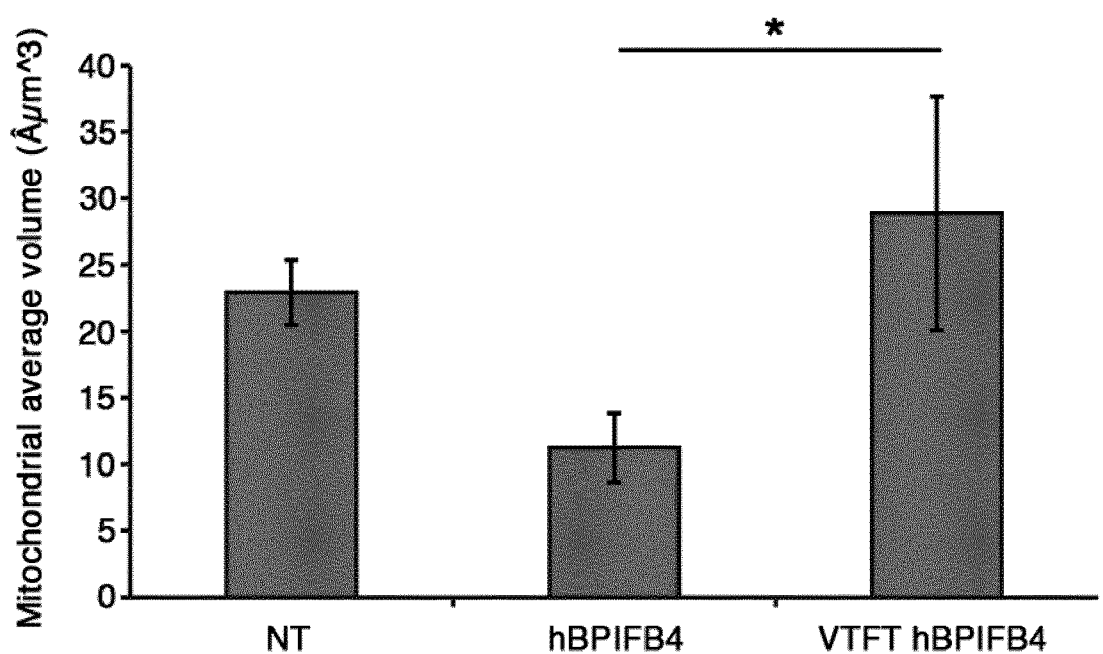

FIG. 3. Mitochondrial average volume evaluation. Histogram shows mitochondrial average volume of human fetal fibroblasts C1-Bio 86 which are not treated (NT) or treated with INLI-hBPIFB4 ("hBPIFB4") or VTFT-hBPIFB4 ("VTFT-hBPIFB4") purified recombinant protein.

Figure 4:
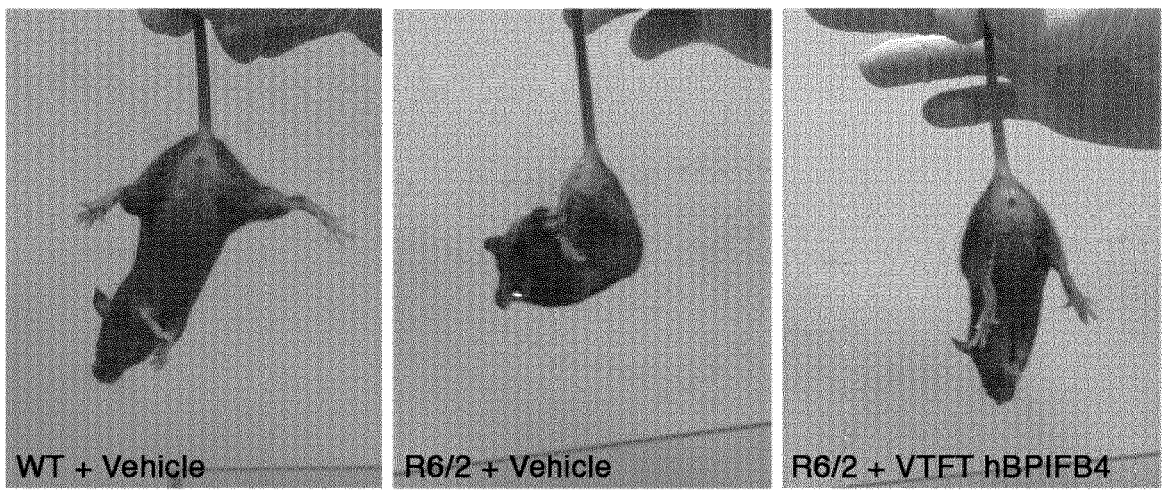
Figure 4:
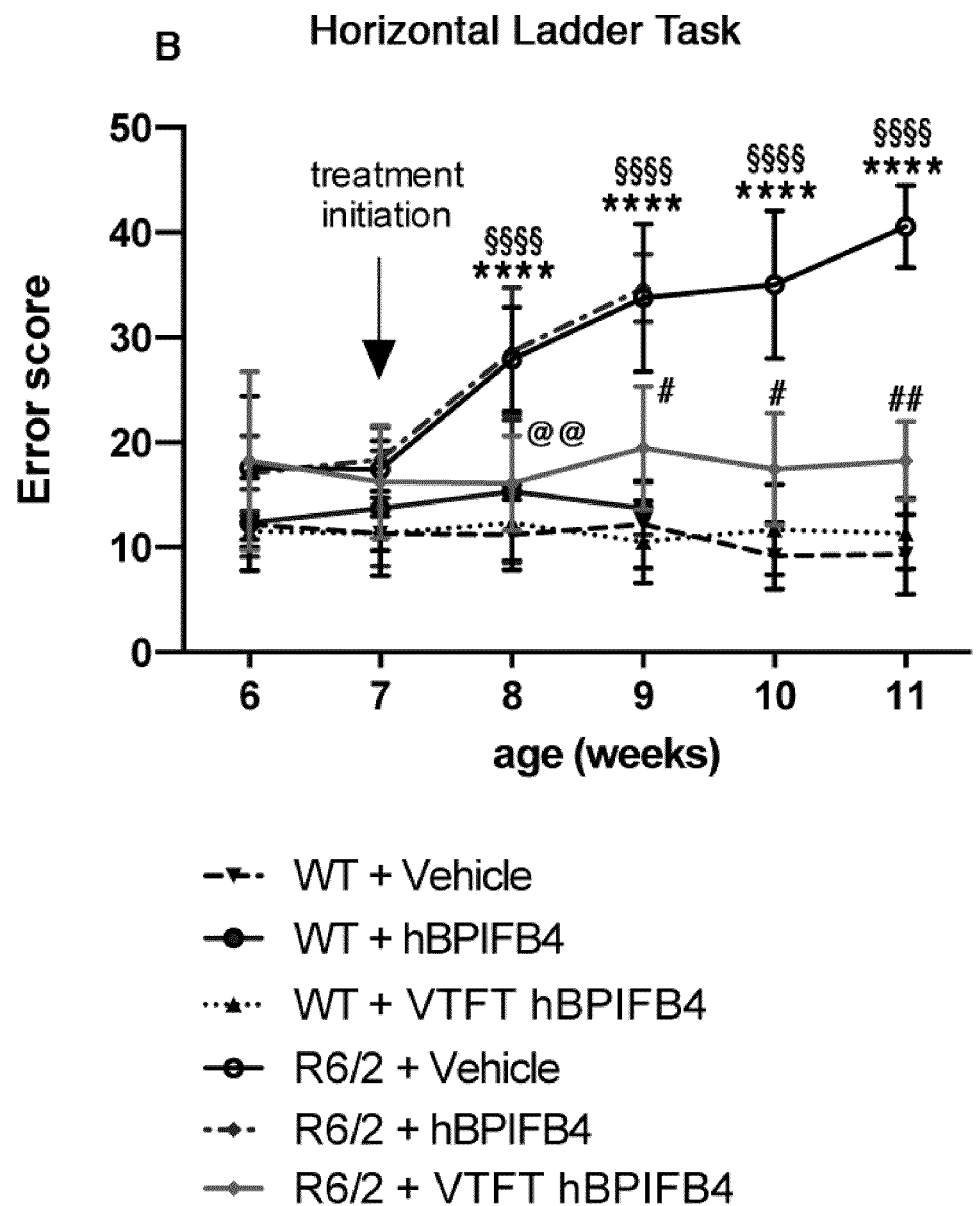
Figure 4:
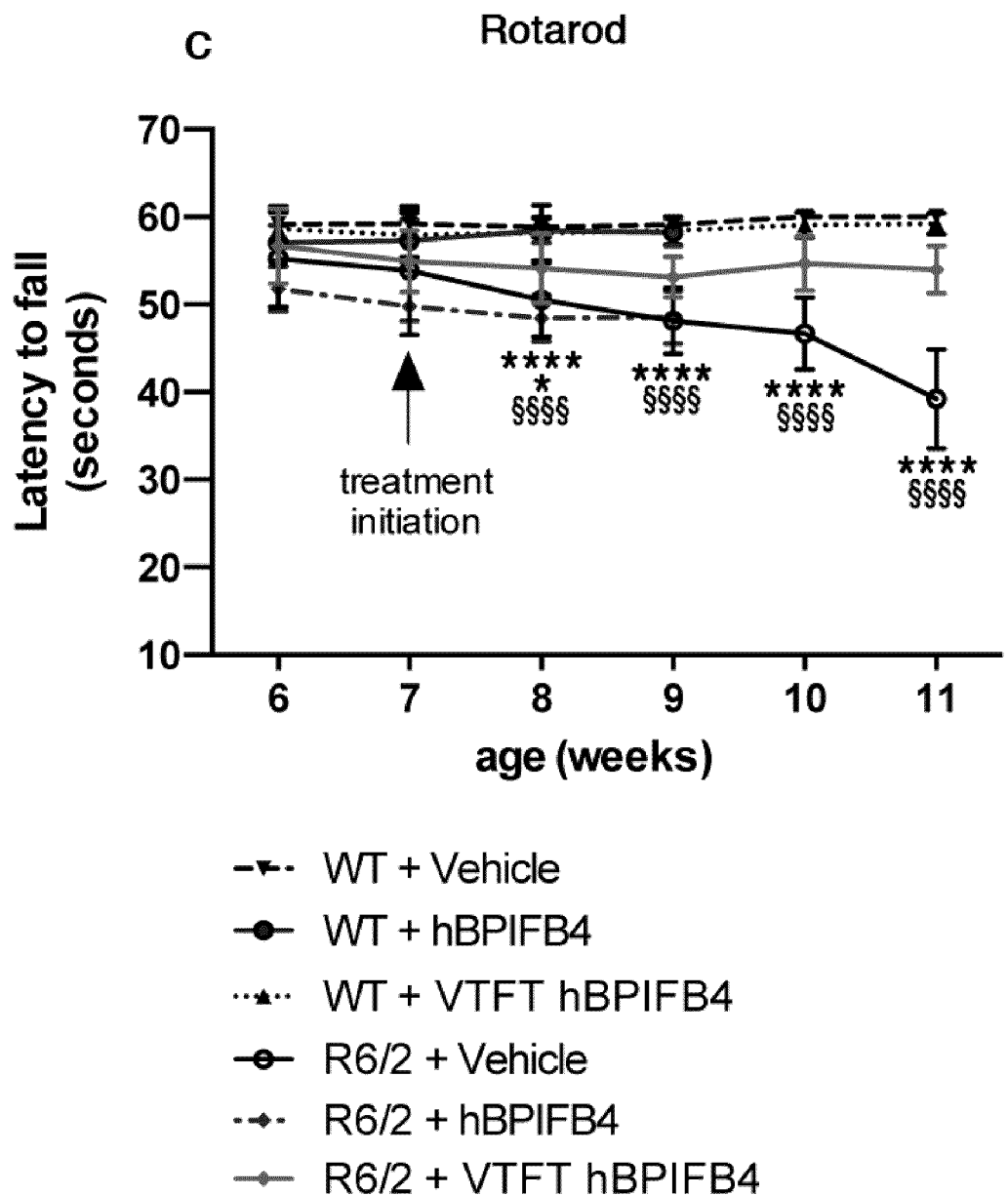
Figure 4:
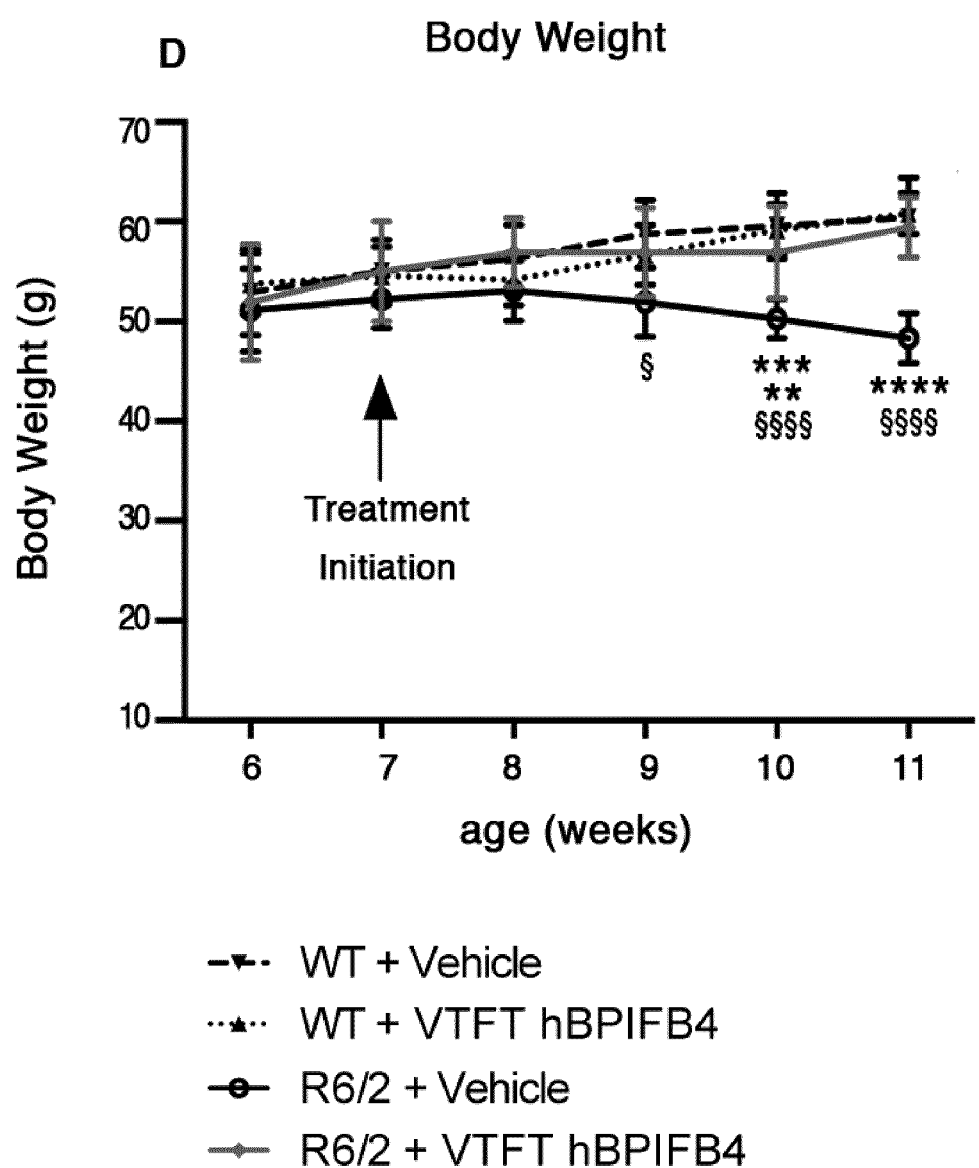
Figure 4:
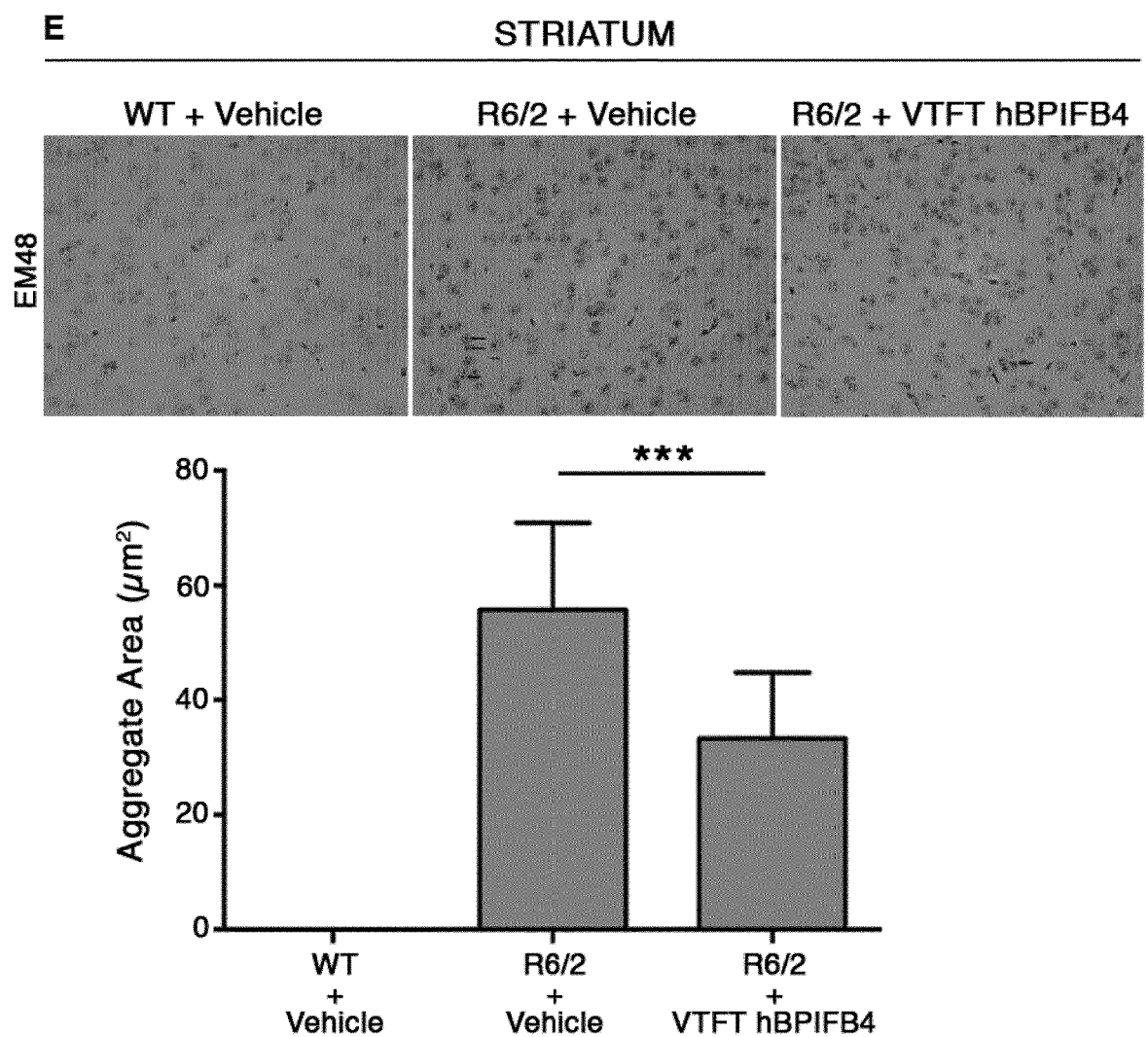

FIG. 4. Overexpression of VTFT-BPIFB4 stops the progression of Huntington's disease and reduces mutant Htt aggregate area in R6/2 mice.

4A Mouse clasping phenotype in mice (wild type ("WT") or R6/2) administered AAV vector carrying VTFT-hBPIFB4 DNA ("VTFT-hBPIFB4") or vector carrying GFP ("Vehicle").

4B-4C Horizontal Ladder Task and Rotarod analyses of motor performance in treated and untreated R6/2 mice and age- and gender-matched wild-type (WT) littermates. Mice were treated with AAV vector carrying VTFT-hBPIFB4 DNA ("VTFT-hBPIFB4"), vector carrying INLI-hBPIFB4 DNA ("hBPIFB4") or vector carrying GFP ("Vehicle"). Each data point represents the average performance±SD of 6-9 mice per group. *, $p<0.05$; ****, $p<0.0001$ (mice injected with AAV vector carrying VTFT-hBPIFB4 DNA vs mice injected with vector carrying GFP). §§§§, $p<0.0001$ (WT mice injected with AAV vector carrying GFP vs R6/2 mice injected with vector carrying GFP). #, $p<0.05$; ##, $p<0.001$ (WT mice injected with AAV vector carrying GFP vs R6/2 mice injected with vector carrying VTFT-hBPIFB4). @@, $p<0.001$ (WT mice injected with AAV vector carrying VTFT-hBPIFB4 vs R6/2 mice injected with vector carrying VTFT-hBPIFB4). 4D Body weight in all groups of mice. Mice were treated with AAV vector carrying VTFT-hBPIFB4 DNA ("VTFT-hBPIFB4") or vector carrying GFP ("Vehicle"). Each data point represents the average of body weight±SD of 6-9 mice. *, $p<0.05$; , $p<0.01$; *, $p<0.001$ (mice injected with AAV vector carrying VTFT-hBPIFB4 DNA vs mice injected with vector carrying GFP). §, $p<0.05$; §§§§, $p<0.0001$ (WT mice injected with AAV vector carrying GFP vs R6/2 mice injected with vector carrying GFP) (two-way ANOVA with Bonferroni post-test). 4E Representative micrographs of striatum, with mutant Htt aggregates revealed by an EM48-specific antibody (upper panels); analysis of affected areas (lower graph). Mice were treated with AAV vector carrying VTFT-hBPIFB4 DNA ("VTFT-hBPIFB4") or vector carrying GFP ("Vehicle").

Figure 5:
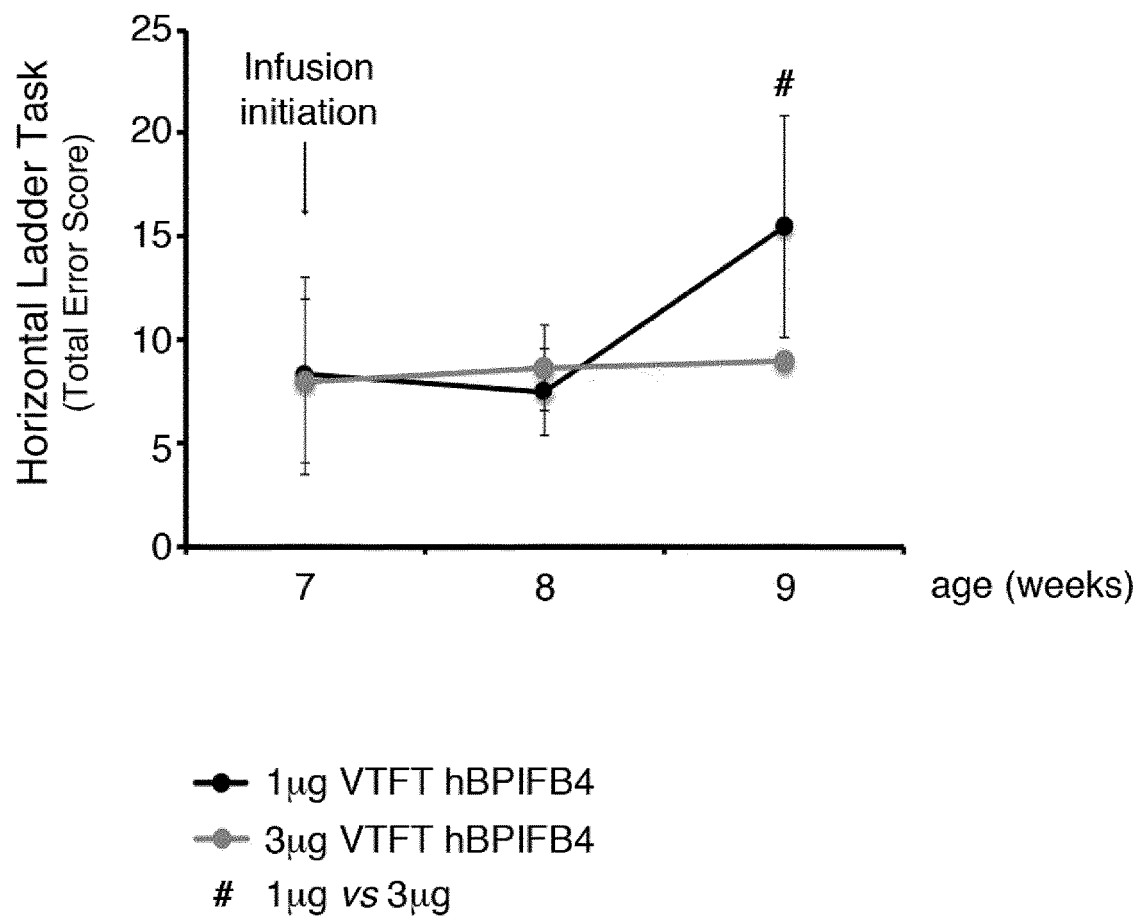

FIG. 5. Oral administration effects of VTFT-hBPIFB4 on Horizontal Ladder Task. Horizontal Ladder Task values of R6/2 mice orally treated with 1 μg or 3 μg VTFT-hBPIFB4 recombinant protein. The infusion of protein was performed by gavage every 3 days starting from the 7th week of animals' age. Values are means±SEM. #, $p<0.05$ R6/2 1 μg vs R6/2 3 μg.

Figure 6:
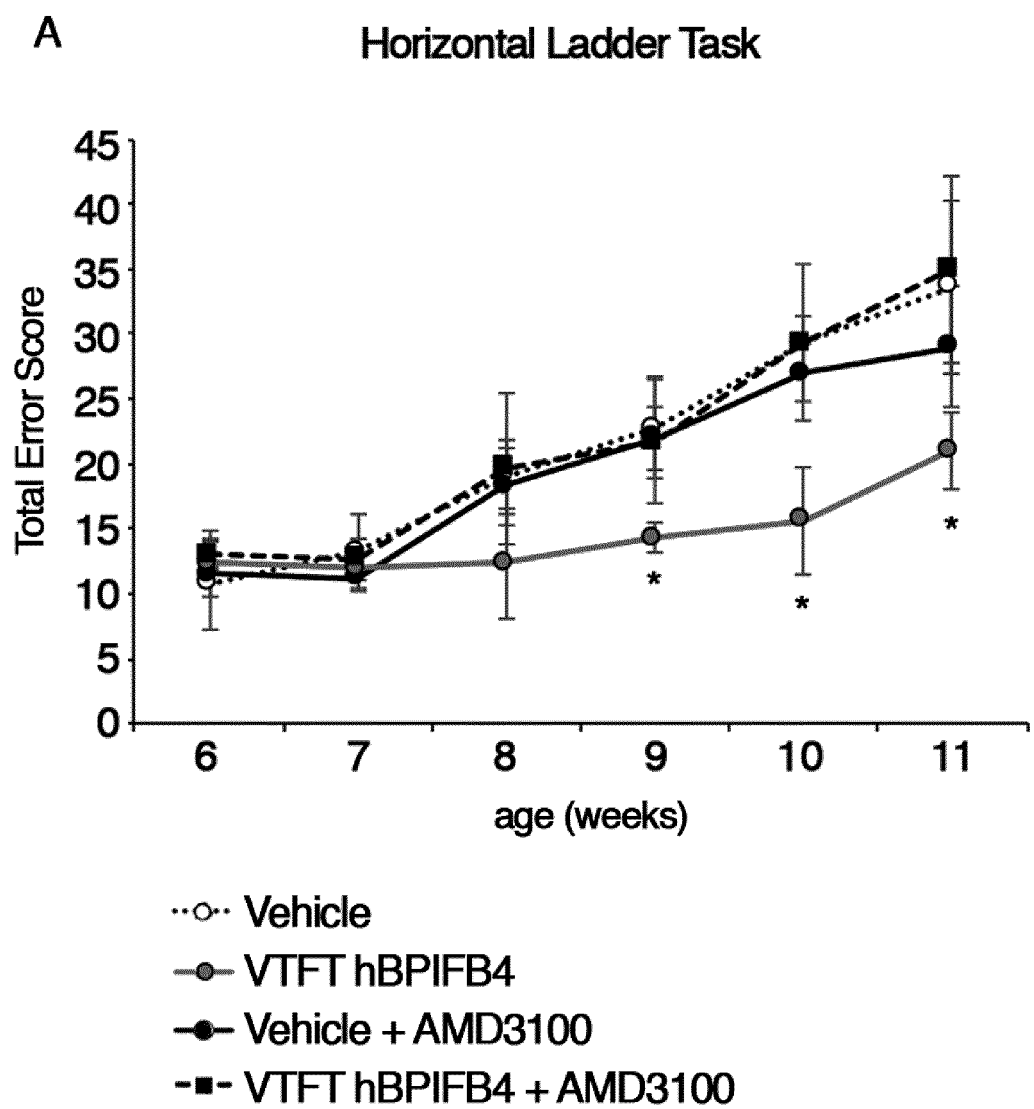
Figure 6:
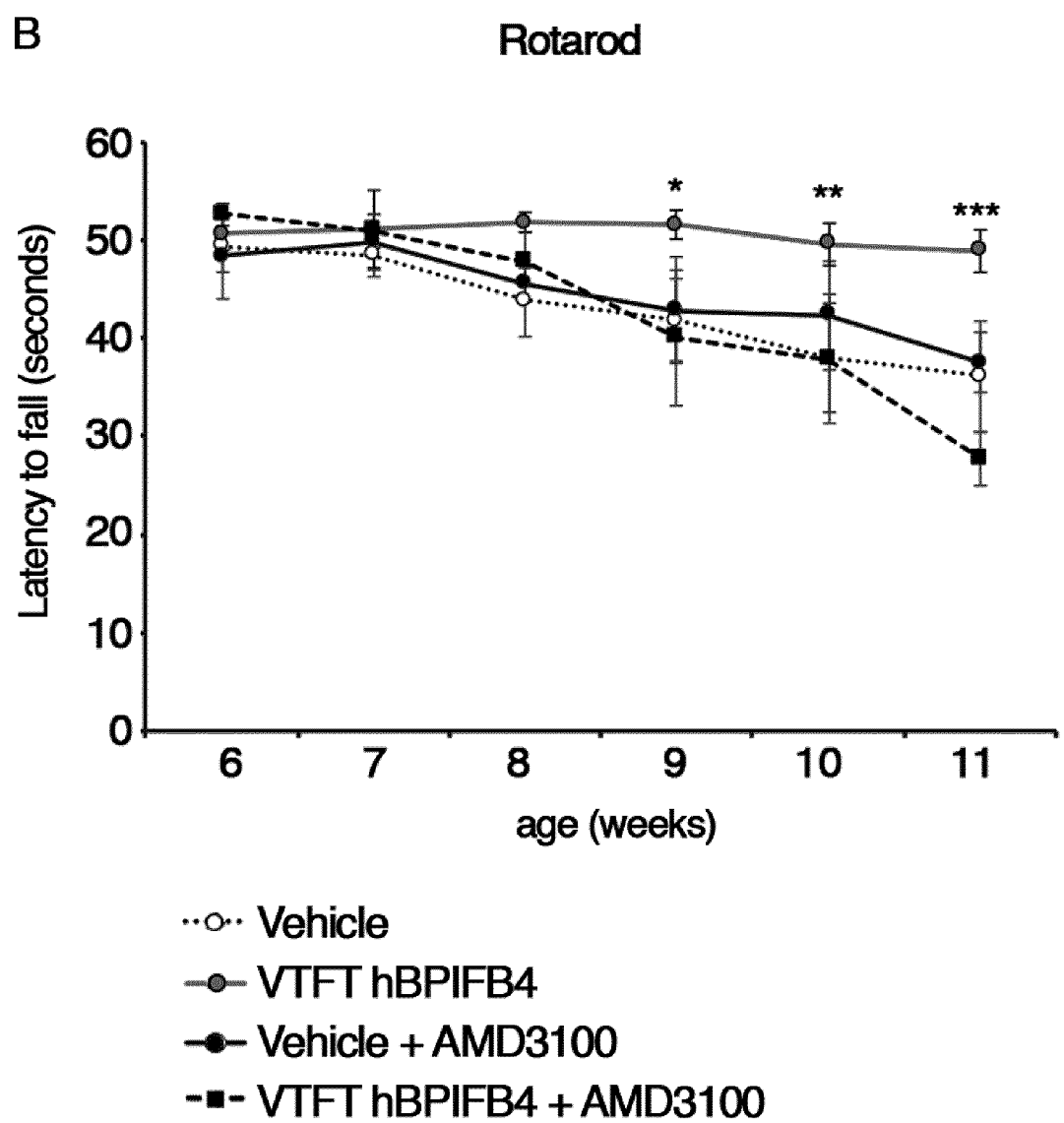
Figure 6:
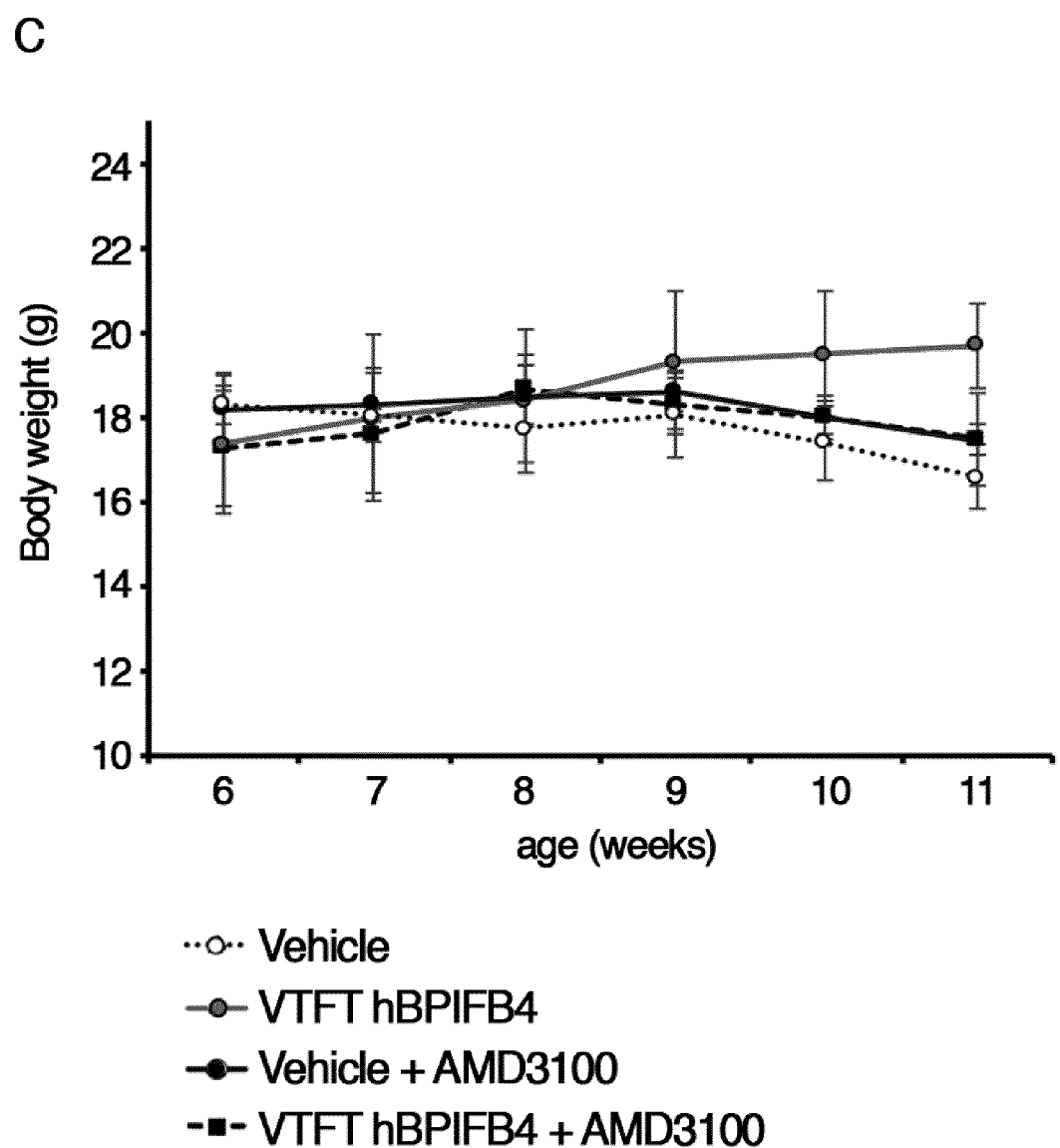

FIG. 6. Motor function improvement by VTFT-BPIFB4 in R6/2 mice is blunted by inhibition of CXCR4.

6A-B Horizontal Ladder Task and Rotarod analyses of motor performance in R6/2 mice injected with AAV vector carrying VTFT-hBPIFB4 DNA or vector carrying GFP ("Vehicle") with or without the CXCR4 inhibitor ADM3100. Each data point represents the average performance±SD of 3-4 mice per group. Unpaired t-test: *, $p<0.05$; , $p<0.01$; *, $p<0.001$ (WT mice injected with AAV vector carrying VTFT-hBPIFB4 vs WT mice injected with AAV vector carrying VTFT-hBPIFB4+AMD3100).

6C Body weight in all groups of mice. Each data point represents the average of body weight±SD of 3-4 mice.

Figure 7:
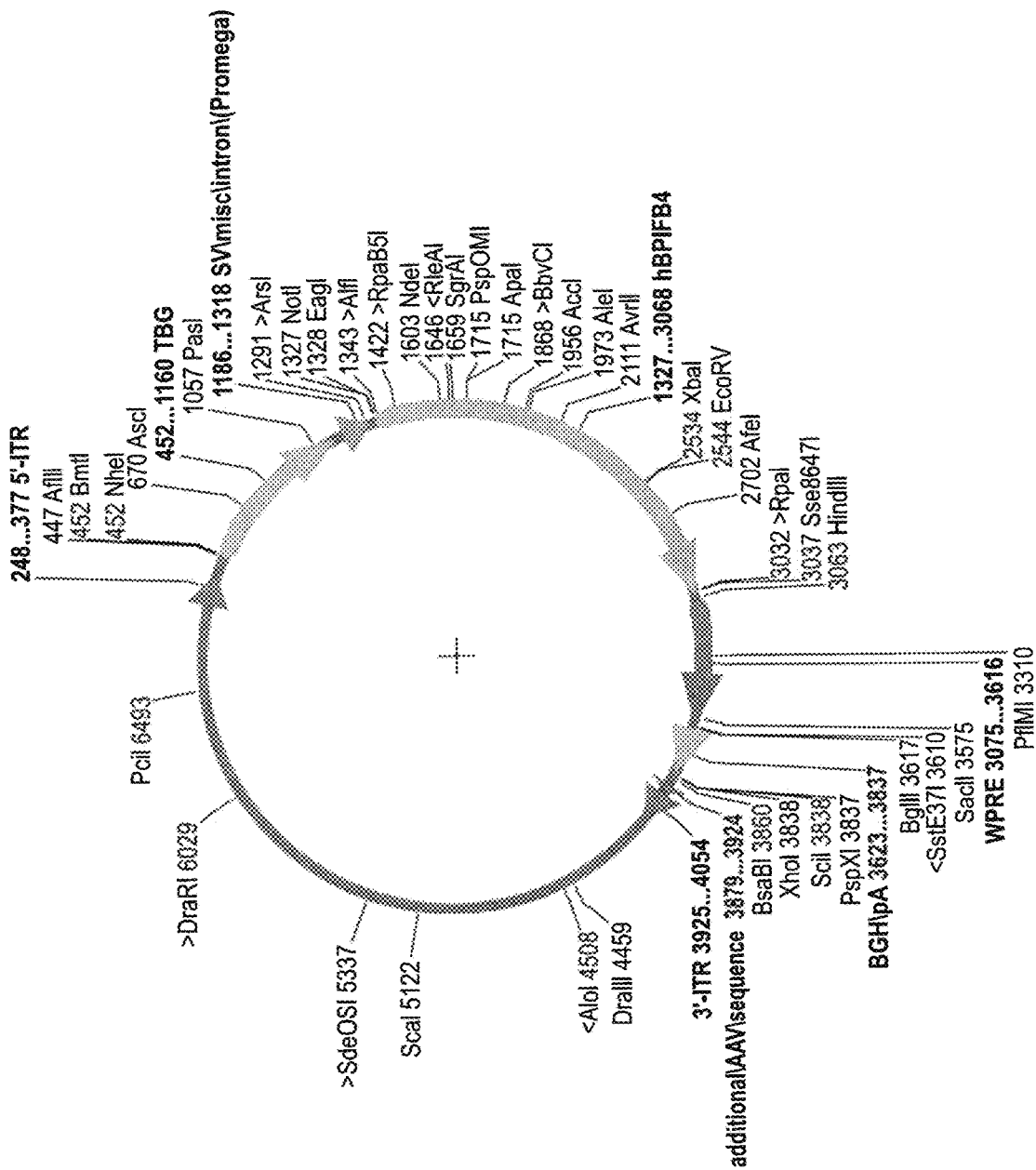

FIG. 7. pAAV2.1 TBG plasmid vector map.

A map of the pAAV2.1 TBG vector with hBPIFB4 sequence cloned between NotI and HindII restriction enzyme sites.

Figure 8:
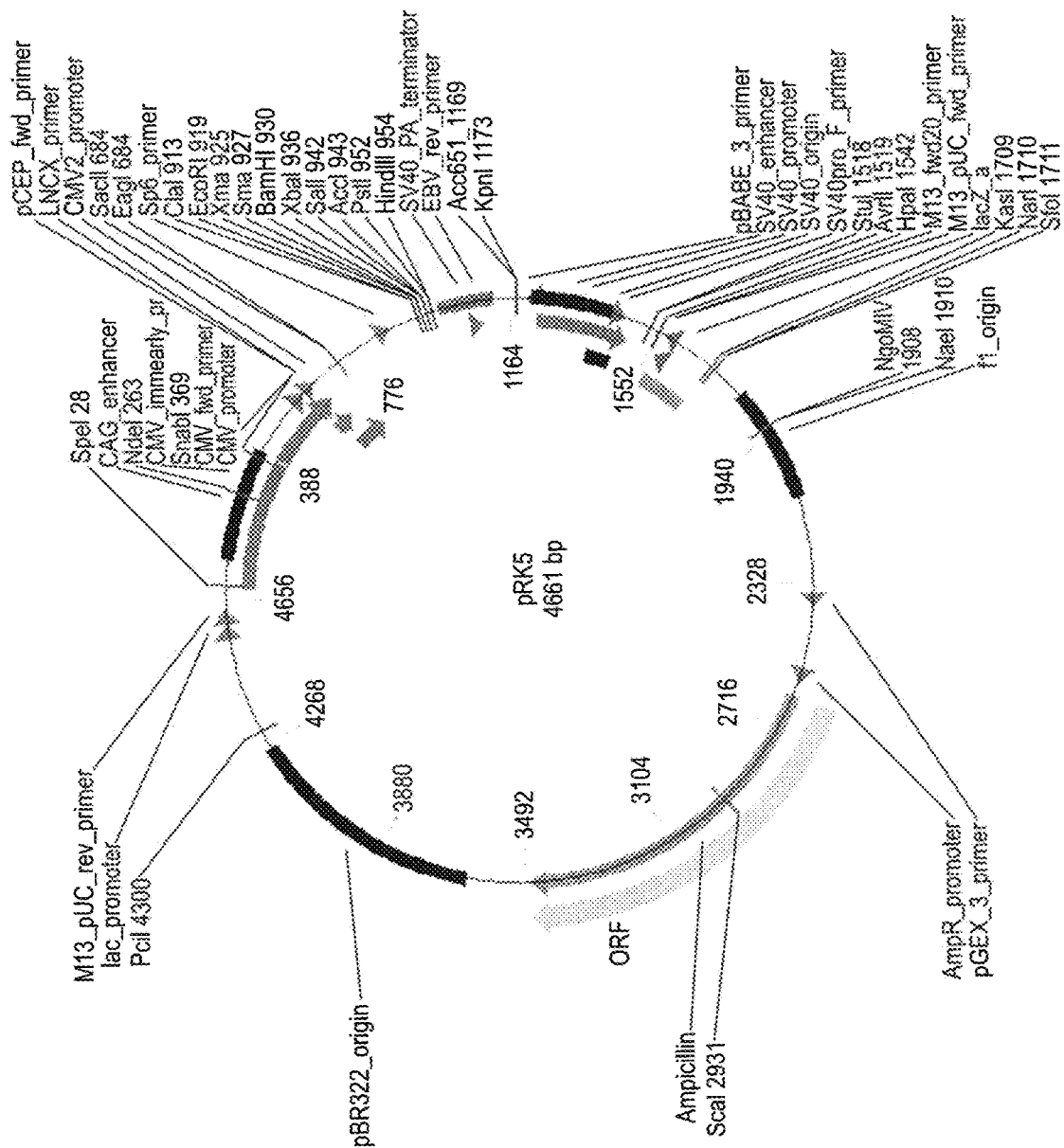

FIG. 8. pRK5 plasmid vector map

A map of the pRK5 plasmid vector used to prepare the constructs employed in Example 1.

Figure 9:
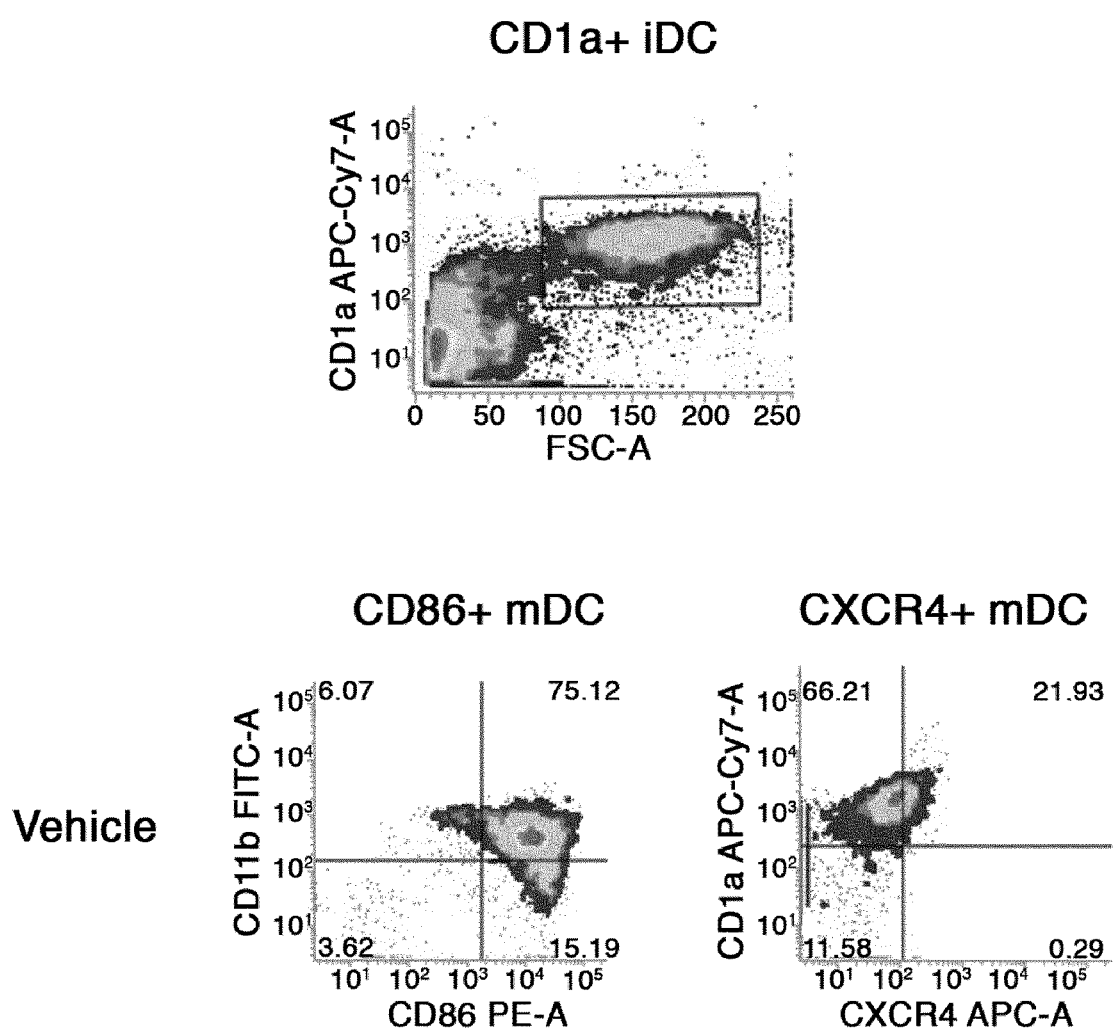
Figure 9:
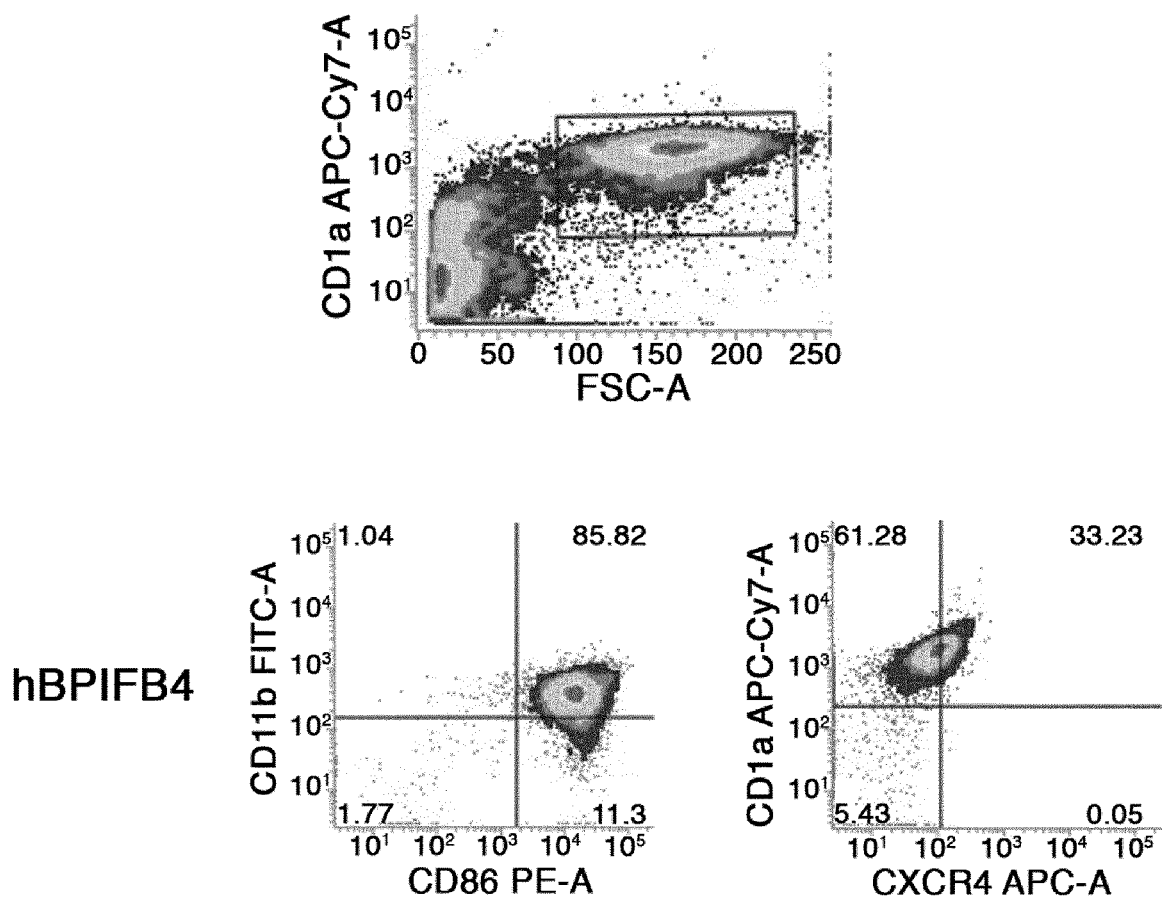
Figure 9:
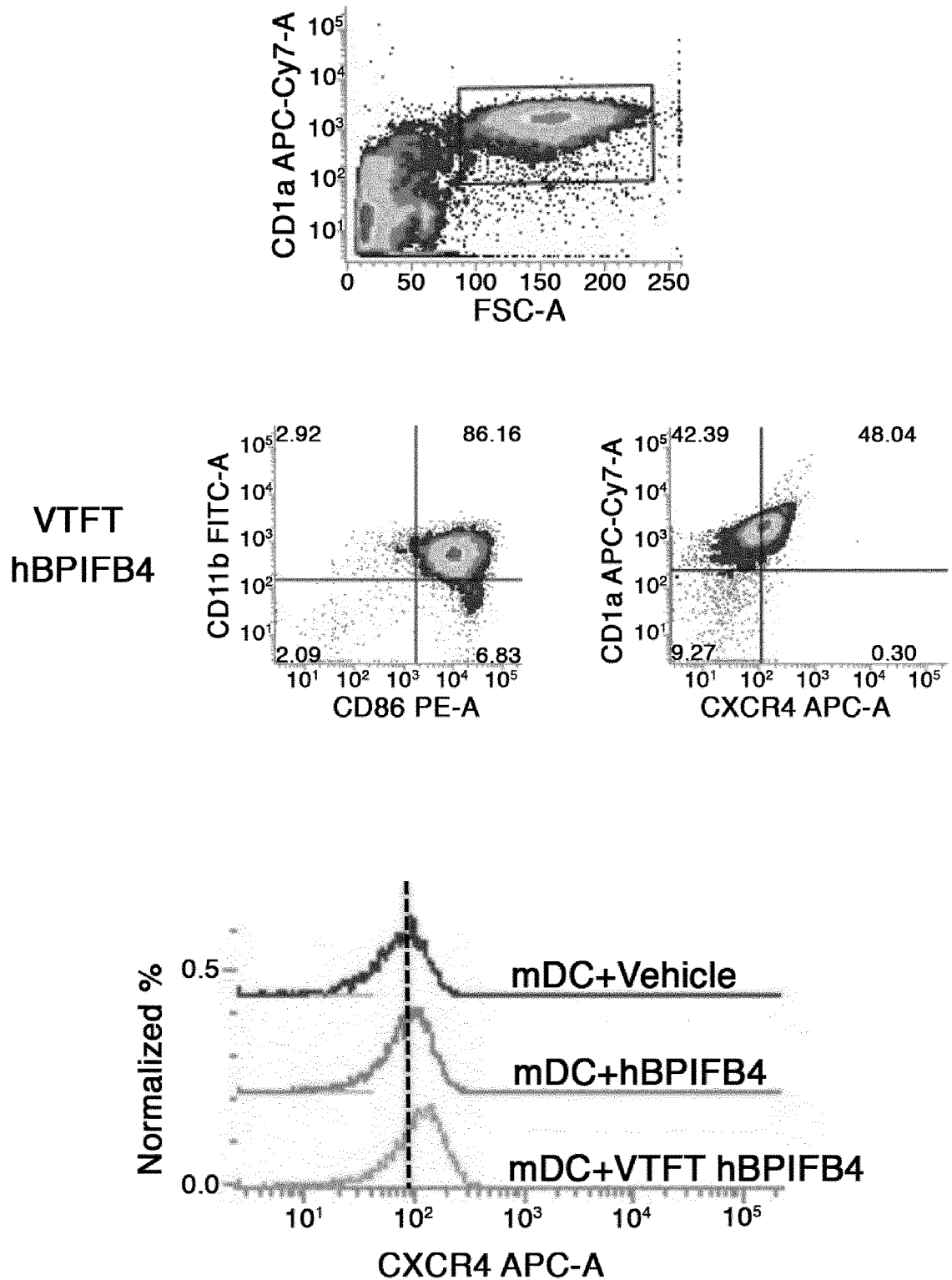

FIG. 9. Evaluation of VTFT-hBPIFB4 effect on generation of monocyte-derived dendritic cells.

FACS analysis of immature monocyte derived dendritic cells (iDCs) cultured with GM-CSF and IL-4, in the presence of a vehicle only ("Vehicle") (FIG. 9 first panel), INLI-hBPIFB4 ("hBPIFB4") (FIG. 9 second panel) or VTFT-hBPIFB4 ("VTFT-hBPIFB4") (FIG. 9 third panel). After 6-8 d, cells were terminally differentiated with LPS and stained with conjugated mAbs against CD14, CD1a, CD86 and CXCR4 before analysis by flow cytometry. Normalised results are shown below FIG. 9 third panel.

BRIEF DESCRIPTION OF THE SEQUENCES IN THE SEQUENCE LISTING

SEQ ID No: 1 Amino acid sequence of the VTFT isoform of a BPIFB4 protein.
SEQ ID No: 2 cDNA sequence encoding the protein of SEQ ID No. 1.

Definitions

"VTFT-hBPIFB4" refers to the protein of SEQ ID No. 1 in which positions 229, 281, 488 and 494 are VTFT respectively. "AAV-VTFT-hBPIFB4" is a plasmid vector encoding TFT-hBPIFB4 (see Examples).

"INLI-hBPIFB4" refers to a protein corresponding to that of SEQ ID No. 1 (Acc. N. NP-59827.2) in which positions 229, 281, 488 and 494 are INLI respectively. This is the predominant isoform of hBPIFB4 in human populations.

A "BPIFB4 protein" refers to the protein of SEQ ID No. 1 and homologues thereof and isoforms thereof; and functionally equivalent variants thereof.

"GFP" means green fluorescent protein.

The term "homologue" as used herein, refers to the amino acid sequence of known BPIFB4 proteins identified in *Homo sapiens* (Acc. N. NP-872325.2, corresponding to a longer isoform than that of SEQ ID No. 1), as well as sequences homologous to SEQ ID No. 1 from other animal species, including but not limited to: *Felis catus* (Acc N. XP003983665.1); *Pan troglodytes* (Acc N XP525303); *Samiri boliviensis boliviensis* (Acc N XP-003932113.1); *Macaca mulatta* (Acc N NP-001230192.1); *Pan paniscus* (Acc. N. XP-003814776.1); *Otolemur garnettii* (Acc N. XP_003788148.1); *Pongo abelii* (Acc N XP-003780649.1); *Sarcophilus harrisii* (Acc N. XP-003758987.1); *Rattus norvegicus* (Acc N. NP-001102679.2); *Callithrix jacchus* (Acc N. XP-003732841.1); *Mus musculus* (Acc N. NP-001030047.2); *Bos taurus* (Acc N XP-003586861.1); *Canis lupus familiaris* (Acc N. XP-534383.3); Susscrofa (Acc N. XP-003134448.3); *Gallus gallus* (Acc No XP-425718), *Didelphis virginiana* (LOC100032880) and *Xenopus* (LOC100485776).

A "VTFT isoform of a BPIFB4 protein" means a BPIFB4 protein which has a Valine residue at the position corresponding to position 229 of SEQ ID No:1, a Threonine residue at the position corresponding to position 281 SEQ ID No: 1, a Phenylalanine residue at the position corresponding to position 488 of SEQ ID No: 1 and a Threonine residue at the position corresponding to position 494 of SEQ ID No: 1.

The term "functionally equivalent" referring to a variant of the protein of SEQ ID NO. 1 or a homologue thereof refers to an amino acid sequence which may differ from that of SEQ ID NO. 1 or a homologue thereof due the presence of additions, deletions of substitutions of amino acids and retains a similar biological activity. Typically, such biological activity will be an activity selected from the activities of increasing mitochondrial function, reducing protein aggregation and increasing CXCR4 activity. Amino acid substitutions are preferably substitutions by a conserved amino acid. By a "conserved amino acid" it is meant an amino acid with functionally physicochemical properties equivalent to those of the original amino acid. Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* 1984).

The term "functional fragment" as used herein refers to an amino acid sequence that has fewer amino acids than the entire sequence of the VTFT isoform of the BPIFB4 protein and is functionally equivalent i.e. it retains a similar biological activity. A functional fragment of the present invention comprises at least the minimum active sequence ranging from amino acids corresponding to positions 75 to 494 of SEQ ID No 1. Functional fragments may, for example, comprise (i.e. be of length at least) 419 residues, e.g. 430 residues, e.g. 450 residues, e.g. 460 residues, e.g. 500 residues, e.g. 550 residues.

The term "disease" is meant in its broadest understanding and encompasses disease, disorder, condition and syndrome.

The term "treatment" means to alleviation of disease or symptoms of disease. It will be understood that in the case of treatment of a genetic disorder (such as Down syndrome) "treatment" refers to alleviation of symptoms of the condition. Treatment includes treatment alone or in conjunction with other therapies. Treatment embraces treatment leading to improvement of the disease or its symptoms or slowing of the rate of progression of the disease or its symptoms.

The term "prophylaxis" means prevention of disease or symptoms of disease and in other respects is to be interpreted as for "treatment".

The term "effective amount" refers to an amount effective, at dosages and for periods of time necessary, to achieve the desired therapeutic (or prophylactic) result, in which any toxic or detrimental effects of the pharmacological agent are outweighed by the therapeutically or prophylactically beneficial effects. It is understood that the effective dosage will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

As used herein, a "subject" is any mammal, including but not limited to humans, non-human primates, farm animals such as cattle, sheep, pigs, goats and horses; domestic animals such as cats, dogs, rabbits; laboratory animals such as mice, rats and guinea pigs that exhibit at least one symptom associated with a disease, have been diagnosed with a disease, or are at risk for developing a disease. The term does not denote a particular age or sex. Suitably the subject is a human subject.

The terms "identical" or "percent identity" in the context of two or more nucleic acids or polypeptide sequences, refer to two or more sequences or sub-sequences that are the same or have a specified percentage of amino acid residues or nucleotides that are the same (i.e., 85%, 90%, 95%, 96%, 97%, 98% or 99% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length. Suitably, the comparison is performed over a window corresponding to the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, references to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-

153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

It must be noted that, as used in this specification and the appended claims, the singular forms "a," "an" and "the" include plural referents unless the context clearly dictates otherwise. Thus, for example, "a dosage form" refers not only to a single dosage form but also to a combination of two or more different dosage forms, "an active agent" refers to a combination of active agents as well as to a single active agent, and the like.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

DETAILED DESCRIPTION OF THE INVENTION

The invention relates to a protein which is a VTFT isoform of a BPIFB4 protein or a functional fragment thereof for use in the treatment or prophylaxis of a condition selected from neuronal diseases and injuries, said diseases and injuries being associated with mitochondrial dysfunction and/or protein aggregation and/or ameliorated by CXCR4 activation.

In an embodiment, the protein comprises or consists of a sequence that has 85%, 90%, 95%, 96%, 97%, 98% or 99% sequence identity to SEQ ID NO: 1, or a homologue thereof (and especially SEQ ID No. 1) wherein said sequence comprises a Valine at the position corresponding to position 229 of SEQ ID NO: 1, a Threonine at the position corresponding to position 281 SEQ ID NO: 1, a Phenylalanine at a position corresponding to position 488 of SEQ ID NO: 1 and a Threonine at position corresponding to position 494 of SEQ ID NO: 1, and is functionally equivalent to the protein of SEQ ID NO: 1 or is a functional fragment thereof.

In an embodiment, VTFT isoform of the BPIFB4 protein has 50, 40, 30, 20, 15, 10, 5, 2 or 1 amino acid additions, deletions or substitutions relative to the sequence of SEQ ID NO: 1 (not being additions, deletions or substitutions at positions corresponding to positions 229, 281, 488 and 494 of SEQ ID No. 1. Preferably substitutions are conservative substitutions. Preferably there are no additions, deletions or substitutions at positions corresponding to positions 75 and 92 of SEQ ID No. 1 (which are Serine and Serine respectively).

Suitably, VTFT isoform of a BPIFB4 protein of the invention comprises, e.g. consists of, the amino acid sequence of SEQ ID NO: 1.

In an alternative embodiment, the VTFT isoform of a BPIFB4 protein of the invention has an amino acid sequence corresponding to the sequence of SEQ ID NO: 1, wherein one or more (e.g. 1, 2, 3, 4, 5, 6, 7, 8, 9 or 10) amino acids at positions different from positions 229, 281, 488 and 494 of SEQ ID NO 1 have been substituted by a different amino acid especially a conserved amino acid.

In an embodiment, the VTFT isoform of a BPIFB4 protein of the invention has an amino acid sequence corresponding to the sequence of SEQ ID NO: 1, wherein one or more (e.g. 1, 2, 3, 4, 5, 6, 7, 8, 9 or 10) amino acids at positions different from positions 75, 82, 229, 281, 488 and 494 of SEQ ID NO 1 have been substituted by a different amino acid especially a conserved amino acid.

A functional fragment of a VTFT isoform of a BPIFB4 protein of the invention may comprise residues 75 to 494 of SEQ ID NO. 1 or of a sequence with amino acid substitutions as described in the previous two paragraphs.

In an embodiment, the VTFT isoform of a BPIFB4 protein or the functional fragment thereof has the function of increasing mitochondrial function e.g. as indicated by having activity in increasing OCR and/or mitochondrial volume. OCR and/or mitochondrial volume may be measured as explained in Example 1.

In an embodiment, the VTFT isoform of a BPIFB4 protein or the functional fragment thereof has the function of having activity in reducing protein aggregation. Reducing protein aggregation may be measured by immunohistochemistry as described in Example 2.

In an embodiment, the VTFT isoform of a BPIFB4 protein or the functional fragment thereof has the function of increasing CXCR4 activity (e.g. by improving CXCR4 localization to cytoplasmic membrane). Increased CXCR4 activity may be measured by measuring its presence at the cytoplasmic membrane level, via techniques such as fluorescence imaging (see for example, E. Beletkaia. et al., (2016)).

According to an aspect of the present invention, a VTFT isoform of a BPIFB4 protein or functional fragment thereof is administered as a recombinant protein.

The invention further provides a polynucleotide encoding a VTFT isoform of a BPIFB4 protein or functional fragment thereof and a vector, preferably a gene therapy vector, containing said polynucleotide operatively linked to expression control sequences.

Expression of the protein sequence may be driven by a suitable promoter, such as a thyroxine binding globulin (TBG) promoter.

Accordingly, there is provided a polynucleotide encoding a VTFT isoform of a BPIFB4 protein or functional fragment thereof as defined above for use in the treatment or prophylaxis of a condition selected from neuronal diseases and injuries, said diseases and injuries being associated with mitochondrial dysfunction and/or protein aggregation and/or ameliorated by CXCR4 activation.

According to a preferred embodiment, said polynucleotide comprises or consists of the sequence of SEQ ID NO: 2.

Accordingly, there is further provided a vector comprising a polynucleotide encoding a protein which is a VTFT isoform of a BPIFB4 protein or a functional fragment thereof as defined above for use in the treatment or prophylaxis of a condition selected from neuronal diseases and injuries, said diseases and injuries being associated with mitochondrial dysfunction and/or protein aggregation and/or ameliorated by CXCR4 activation Further aspects of the invention relate to a method of treatment or prophylaxis of conditions selected from neuronal diseases and injuries, said diseases and injuries being associated with mitochondrial dysfunction and/or protein aggregation and/or ameliorated by CXCR4 activation, which comprises administering to a subject in need thereof an effective amount of a protein which is a VTFT isoform of a BPIFB4 protein or a functional fragment thereof.

There is also provided a method of treatment or prophylaxis of conditions selected from neuronal diseases and injuries, said diseases and injuries being associated with mitochondrial dysfunction and/or protein aggregation and/or ameliorated by CXCR4 activation, which comprises administering to a subject in need thereof an effective amount of polynucleotide encoding a protein which is a VTFT isoform of a BPIFB4 protein or a functional fragment thereof.

There is also provided a method of treatment or prophylaxis of conditions selected from neuronal diseases and injuries, said diseases and injuries being associated with mitochondrial dysfunction and/or protein aggregation and/or ameliorated by CXCR4 activation, which comprises administering to a subject in need thereof an effective amount of a vector comprising a polynucleotide encoding a protein which is a VTFT isoform of a BPIFB4 protein or a functional fragment thereof.

The present invention provides a pharmaceutical composition comprising the protein or functional fragment of the invention or polynucleotide of the invention or the vector of the invention in combination with one or more pharmaceutically acceptable carriers and excipients.

The protein or functional fragment of the invention or polynucleotide of the invention or the vector of the invention may also be administered in combination with one or more other active ingredients e.g. active ingredients suitable for treating the conditions described herein. For example, possible active ingredients include:

Medicaments for Parkinson's disease such as carbidopa or levodopa, dopamine agonists such as pramipexole, ropinirole, rotigotine or apomorphine; MAO-B inhibitors such as selegiline or rasagiline; catechol-O-methyltransferase (COMT) inhibitors such as entacapone; anticholinergic medications such as benztropine or trihexyphenidyl; or amantadine.

Medicaments for Alzheimer's disease such as cholinesterase inhibitors, such as donepezil, galantamine or rivastigmine; Memantine; monoclonal antibodies such as solanezumab; Fyn inhibitors such as saracatinib; Tau aggregation inhibitors; anti-inflammatory drugs such as pioglitazone.

Medicaments for Huntington's disease such as medications for movement disorders such as tetrabenazine, antipsychotic drugs, such as haloperidol, chlorpromazine, risperidone, olanzapine risperidone or quetiapine; amantadine, levetiracetam, clonazepam; antidepressants such as citalopram, escitalopram, fluoxetine or sertraline; mood-stabilizing drugs including anticonvulsants, such as valproate, carbamazepine or lamotrigine; food supplements such as CoenzymeQ10 or idebenone.

Medicaments for amyotrophic lateral sclerosis include riluzole and edaravone.

In one embodiment the combination of active ingredients are co-formulated.

In one embodiment the combination of active ingredients is co-administered sequentially or simultaneously.

In one embodiment there is provided a combination product comprising:
(A) a protein or functional fragment of the invention or polynucleotide of the invention or the vector of the invention; and
(B) a further active ingredient (as mentioned above)
wherein each of components (A) and (B) is formulated in admixture with pharmaceutically-acceptable diluent(s) or carrier(s). The combination may optionally comprise additional relevant excipients.

In one embodiment there is provided a protein or functional fragment of the invention or polynucleotide of the invention or the vector of the invention for use as a medicament to be administered in combination with one or more further active ingredients (as mentioned above).

The practice of the present invention employs, unless otherwise indicated, conventional methods of molecular biology, microbiology, virology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.)).

It is to be understood that unless otherwise indicated, this invention is not limited to particular dosages, formulations or methods of use, as such may vary. It is also to be understood that the terminology used herein is for the purpose of describing particular embodiments only, and is not intended to be limiting.

Diseases to be Treated or Prevented

The term "neuronal disease" indicates a disease that involves brain, spinal cord, and nerves that make up the nervous system and encompasses "neurodegenerative diseases" and "neuromuscular diseases". Neurological diseases can be due to faulty genes, or they can be degenerative, where nerve cells are damaged or die. Examples of neuronal diseases include Down Syndrome (DS) and Wolfram syndrome (WS).

The term "neurodegenerative disease" refers to an impairment or absence of a normal neurological function or presence of an abnormal neurological function in a subject. For example, neurodegenerative diseases can be the result of disease, injury, and/or aging. It also includes neurodegeneration which causes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, multiple sclerosis, Huntington's disease, Parkinson's disease, Alzheimer's disease, Creutzfeldt-Jakob disease or prion disease.

Scrapie is an example of a neurodegenerative disease particularly affecting sheep and goats particularly associated with abnormal protein aggregation. Bovine spongiform encephalitis is a neurodegenerative disease affecting cows also particularly associated with abnormal protein aggregation.

The term "neuromuscular disease" indicates a disease that affects the muscles and/or their direct nervous system control, problems with central nervous control can cause either spasticity or some degree of paralysis (from both lower and upper motorneuron disorders), depending on the location and the nature of the problem. Some examples of central disorders include cerebrovascular accident, amyotrophic lateral sclerosis (ALS), spinocerebellar ataxia (SCA), Freidreich Ataxia (FA), Mitochondrial Myopathy Encephalopathy, Lactic acidosis with stroke-like episodes (MELAS), Charcot Marie Tooth 2A (CMT 2A) and spinal muscular atrophy (SMA). Spinal muscular atrophies are disorders of lower motor neuron, while amyotrophic lateral sclerosis is a mixed upper and lower motor neuron condition.

Suitably, the condition is selected from multiple sclerosis, Alzheimer's disease (AD), Parkinson's disease (PD), Huntington's disease (HD), Amyotrophic lateral sclerosis (ALS), spinocerebellar ataxia (SCA), in particular SCA1, SCA2, SCA3 (MJD), SCA6, SCA7, SCA17, Freidirich Ataxia (FA), Down Syndrome (DS), Wolfram syndrome (WS), Mitochondrial Myopathy Encephalopathy, Lactic acidosis with stroke-like episodes (MELAS), Charcot Marie Tooth 2A (CMT 2A) and Creutzfeldt-Jakob disease or prion disease.

Suitably, the condition is spinal muscular atrophy (SMA).

The term "neuronal injury" means an injury to the brain and/or central nervous system and the neurons thereof including traumatic injury e.g. spinal cord injury. In connection with neuronal injury such as spinal cord injury, the role of the VTFT isoform of a BPIFB4 protein or a functional fragment thereof in increasing CXCR4 activity is considered to be particularly important (rather than enhancing mitochondrial function or reducing protein aggregation).

Conditions associated with protein aggregation such as Huntington's disease, Alzheimer's disease, Creutzfeldt-Jakob disease and prion disease are of particular interest in the context of the invention.

In a preferred embodiment, the condition of the invention is selected from Down syndrome, Huntington's disease, ALS, PD, AD and SCA.

In a particularly preferred embodiment, the condition is Huntington's disease.

In one embodiment, the VTFT isoform of the BPIFB4 protein or functional fragment thereof is administered through gene therapy to a subject in need of, wherein a nucleotide sequence encoding said variant or fragment thereof is inserted in a vector.

Suitably the vector is selected from adeno-associated viral vectors, adenovirus vectors, herpes virus vectors, parvovirus vectors, and lentivirus vectors; preferably, adeno-associated viral vectors, preferably adeno-associated viral vectors.

Suitably the vector comprises (such as consists of) the nucleotide sequence of SEQ ID NO. 2 or a fragment thereof encoding the VTFT isoform of the BPIFB4 protein.

Suitably adeno-associated viral vectors of the invention include but are not limited to AAV1, AAV2, AAV3, AAV4, AAV5, AAV6, AAV7, AAV8, AAV9, preferably AAV9.

In an alternative embodiment, the recombinant protein of SEQ ID NO. 1 or the functional fragment thereof is administered to a subject in need of.

The protein of the invention is useful in treating humans and other mammals (including domestic animals and livestock such as cows, sheep and goats), particularly humans.

Delivery Systems and Administration Methods

According to a first aspect, the polypeptide of the invention is delivered via gene therapy methods.

In an embodiment of the invention, the polynucleotide of the invention is delivered via a virus e.g. an adeno-associated virus. For example, the polynucleotide of the invention is incorporated into a viral vector e.g. an adeno-associated virus vector.

The adeno-associated virus (AAV) is a replication deficient parvovirus with a single stranded DNA of about 4.7 kb in length which include 145 bp of inverted repeat (ITRs). Cis-acting sequences directing viral replication (rep), encapsidation and packaging and host cell integration are contained within the ITRs. Three AAV promoters, (p5, p29, p40) drive the expression of the open reading frames encoding the rep and cap genes.

AAV possesses unique features which render it optimal for delivery of foreign DNA to cells as in vitro and in vivo, as in gene therapy. AAV infection of cells in culture is non-cytopathic, and natural infection of humans and other animals is asymptomatic and silent. Moreover, AAV infect many mammalian cell types allowing the possibility of targeting different tissues in vivo. Furthermore, AAV transduces slowly dividing or non-dividing cells and can persist for a life time of the infected cells as a transcriptionally active nuclear episome, eg an extra chromosomal element.

In one aspect, the invention therefore provides recombinant AAV ("rAAV") genomes. The rAAV genomes comprise one or more ITRs flanking a polynucleotide encoding a polypeptide of the invention, operatively linked to transcriptional control DNAs, for example promoter DNA, polyadenylation signal sequence DNA that form a gene cassette. The gene cassette may also include intron sequences to facilitate processing of an RNA transcript when expressed in mammalian cells.

In some embodiments, the genome of the AAV vector including the polynucleotide of the invention is a single stranded genome; in alternative embodiments, the genome of the AAV vector including the polynucleotide of the invention is a self-complementary genome, wherein the coding region has been designed to form an intra-molecular double-stranded DNA template; upon infection, the two complementary halves of self-complementary AAV will associate to form one double stranded DNA (dsDNA) unit that is ready for immediate replication and transcription.

Multiple serotypes of AAV viruses are available, with different tissue tropism such as AAV1, AAV2, AAV3, AAV4, AAV5, AAV6, AAV7, AAV8, AAV9, AAV10, AAV11.

The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC 001401; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al, (2004) and in U.S. Pat. No. 7,198,951 incorporated herein by reference; the AAV-10 genome is provided in De. et al., Mol. Ther., (2006) 13(1): 67-76; and the AAV-11 genome is provided in Mori, et al., Virology, (2004) 330(2): 375-383.

In another aspect, the invention provides DNA plasmids comprising rAAV genomes of the invention. The DNA plasmids are transferred to cells permissible for infection with a helper virus of AAV (e.g., adenovirus, El-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. AAV capsid proteins may be modified to enhance delivery of the recombinant vector. Modifications to capsid proteins are generally known in the art.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing, addition of synthetic linkers containing restriction endonuclease cleavage sites or by direct, blunt-end ligation. The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

Delivery of the rAAV carrying the polynucleotide of the invention can be in vivo or ex vivo; with a pharmaceutically suitable carrier.

The vector can be distributed throughout a wide region of the CNS, by injecting the vector into the cerebrospinal fluid, e.g., by lumbar puncture.

Alternatively, precise delivery of the vector into specific sites of the brain, can be conducted using stereotactic microinjection techniques. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular or subcutaneous injection. In another embodiment, the vector is administered orally. In the most preferred embodiment, the vector is delivered to a specific location using stereostatic delivery.

Delivery of AAV viruses to skeletal and cardiac muscles is possible through systemic or intramuscular injections.

Delivery of AAV viruses within the central nervous system requires surgical intraparenchimal injection. However, as detailed in WO2010071832 incorporated herein by reference, rAAV9 vectors can be delivered systemically access the blood brain barrier. In some embodiments, the polynucleotide of the invention is delivered to the brain. In other embodiments, the polynucleotide is delivered to the spinal cord. In still other embodiments, the polynucleotide is delivered to neurons, motor neurons and/or to glial cells. In some aspects, the glial cell is a microglial cell, an oligodendrocyte or an astrocyte. In other aspects the polynucleotide is delivered to a Schawn cell.

In a preferred embodiment of the invention, the polynucleotide of the invention is incorporated in a rAAV9 virus. In a particularly preferred embodiment, the sequence of the vector as illustrated in FIG. 7.

In a further embodiment, the polynucleotides of the invention are delivered via non-viral delivery such as colloidal dispersion systems that include, for example, macromolecule complexes, nanocapsules, microspheres, beads, and lipid-based systems including oil-in-water emulsions, micelles, mixed micelles, and liposomes.

Alternatively, the polynucleotides of the invention are suitably coupled with a carrier for delivery, preferably keyhole limpet hemocyanin (KLH) and human serum albumin. Other carriers may include a variety of lymphokines and adjuvants such as INF, IL-2, IL-4, IL-8 and others. Means for conjugating a peptide to a carrier protein are well known in the art and include glutaraldehyde, m-maleimidobenzoyl-N-hydroxysuccinimide ester, carbodiimyde and bis-biazotizedbenzidine.

According to a second aspect of the invention, the polypeptide of the invention is delivered as a recombinant protein. The recombinant protein is suitably administered intrathecally, intraperitoneally, intravenously, intra-arterially or orally.

Several key approaches for brain targeting include physiological transport mechanisms such as adsorptive-mediated transcytosis, inhibition of active efflux pumps, receptor-mediated transport, cell-mediated endocytosis, and the use of peptide vectors. Drug-delivery approaches comprise delivery from microspheres, biodegradable wafers, and colloidal drug-carrier systems (e.g., liposomes, nanoparticles, nanogels, dendrimers, micelles, nanoemulsions, polymersomes, exosomes, and quantum dots). Adsorptive mediated transcytosis (AMT) involves electrostatic binding of polycationic peptides or proteins, acting as ligands, with microanionic moieties present at the luminal surface of the endothelial cells. Although AMT has lower binding affinities than RMT, it allows for higher binding capacities. Cationized albumin is an example of such a ligand, which was reported to be conjugated with deferasirox, an iron chelating agent, for Alzheimer's disease; cationic bovine serum albumin was conjugated to engineered solid lipid nanoparticles (SLNs) containing the anti-cancer agent doxorubicin, depicting maximum transcytosis of the developed system to HNGC-1cell lines and improved pharmacokinetics using the in-vivo system GM1 is a glycosphingolipid that is ubiquitously present on the endothelial surface and capable of acting as the transcytotic receptor for cholera toxin B. Ganglioside P-gpP-glycoprotein.

Further Embodiments

According to further embodiments of the invention there are provided:
A protein which is a VTFT isoform of a BPIFB4 protein or a functional fragment thereof for use in the treatment or prophylaxis of a condition selected from neuronal diseases and injuries, said diseases and injuries being associated with mitochondrial dysfunction and/or protein aggregation. There is also provided a polynucleotide encoding such protein and a vector comprising such polynucleotide.
A protein which is a VTFT isoform of a BPIFB4 protein or a functional fragment thereof for use in the treatment or prophylaxis of a condition selected from Alzheimer's disease, Parkinson's disease, Huntington's disease, Amyotrophic lateral sclerosis, spinocerebellar ataxia (SCA), in particular, SCA1, SCA2, SCA3, SCA6, SCA7, SCA17, Freidirich Ataxia, Down Syndrome, Wolfram syndrome, Mitochondrial Myopathy Encephalopathy, Lactic acidosis with stroke-like episodes, Charcot Marie Tooth 2A, Creutzfeldt-Jakob disease or prion disease and spinal muscular atrophy; especially selected from Down syndrome, Huntington's disease, Amyotrophic lateral sclerosis, Parkinson's disease, Alzheimer's disease and spinocerebellar ataxia, preferably Huntington's disease; and particularly Huntington's disease. There is also provided a polynucleotide encoding such protein and a vector comprising such polynucleotide.
A protein which is a VTFT isoform of a BPIFB4 protein or a functional fragment thereof for use in the treatment or prophylaxis of spinal cord injury. There is also provided a polynucleotide encoding such protein and a vector comprising such polynucleotide.

EXAMPLES

Hereinafter, the present invention is described in more detail and specifically with reference to the Examples, however these are not intended to limit the present invention.

Materials

Where AAV-VTFT-hBPIFB4 is referred to in the Examples, this was constructed as shown in FIG. 7. Where AAV-GFP is referred to, this was constructed as shown in FIG. 7 with substitution of a GFP sequence for the hBPIFB4 sequence.

The pRK5 Empty Vector (EV) was constructed from the plasmid vector shown in FIG. 8 with a GFP sequence inserted after the Kpn1 (1173) restriction site.

The pRK5 VTFT-hBPIFB4 vector was constructed from the plasmid vector shown in FIG. 8 with a VTFT-hBPIFB4 sequence inserted between the HindIII (954) and Kpn1 (1173) restriction sites and a GFP sequence inserted after the Kpn1 (1173) restriction site.

Example 1—Effect of VTFT-hBPIFB4 Vector on Cellular Metabolism

In order to establish how VTFT-hBPIFB4 would impact cellular metabolism, the bioenergetic profile of HEK293T cells transfected with pRK5 Empty Vector (EV) or pRK5 VTFT-hBPIFB4 (VTFT-hBPIFB4) were measured.

The metabolic profile was evaluated in HEK293T cells 72 h after transfection with EV or VTFT-hBPIFB4 encoding pRK5 plasmid.

Indices of mitochondrial respiratory function were calculated from OCR profile: basal OCR (before addition of oligomycin), and ATP-linked OCR (calculated as the difference between basal OCR rate and oligomycin-induced OCR rate).

Indices of glycolytic pathway activation were calculated from ECAR profile: basal ECAR (after the addition of glucose), and glycolytic capacity (calculated as the difference of oligomycin-induced ECAR and 2-DG-induced ECAR).

Data are expressed as mean±s.e.m. from 2 separate experiments. n=5 replicated per sample. Two tailed unpaired t-test was used for statistical analysis.
Metabolism Assays: Oxygen consumption rates (OCR) and extracellular acidification rates (ECAR)

OCR and ECAR were measured in XF media (nonbuffered RPMI medium 1640 containing 10 mM glucose, 2 mM L-glutamin, and 1 mM sodium pyruvate), under basal conditions and in response to 5 μM oligomycin, or 1 mM of 2-DG, using the XF-24 or XF-96 Extracellular Flux Analyzer (Seahorse Bioscience, North Billerica, MA, USA).

Data are expressed as mean±s.e.m. from 2 separate experiments. n=5 replicated per sample. Unpaired t-test two tails was used for statistical analysis.
Mitochondrial Volume Evaluation The cells were seeded at a density of 50,000 cells per well onto 25-mm glass coverslips, allowed to grow for 24 h and then infected with mitochondria-targeted GFP inserted into an adenoviral vector (Ad-mtGFP Ex/Em: 495/515). Protein expression was then allowed for 72 h in the presence of hBPIFB4, VTFT-hBPIFB4 or alone. Coverslips were placed in an incubated chamber with controlled temperature, $CO_2$ and humidity. Single cells were imaged by using a Nikon Swept Field Confocal microscope (Nikon Instruments Inc.)

equipped with a CFI Plan Apo VC60XH objective and an Andor DU885 EM-CCD camera, which was controlled by NIS Elements 3.2. Fifty-one-plane z-stacks were acquired with voxel dimensions of 133×133×200 nm (X×Y×Z). The mitochondrial network was then described in numbers of objects, total volume and object volume using the 3D object counter available in the software Fiji.

Results $O_2$ consumption rate (OCR, FIG. 1A) is an indicator of oxidative phosphorylation (OXPHOS)—the activity of metabolic pathway in which cells use enzymes to oxidize nutrients, thereby releasing energy which is used to reform ATP—and extracellular acidification rates (ECAR, FIG. 2A), an indicator of aerobic glycolysis.

Figure 1:
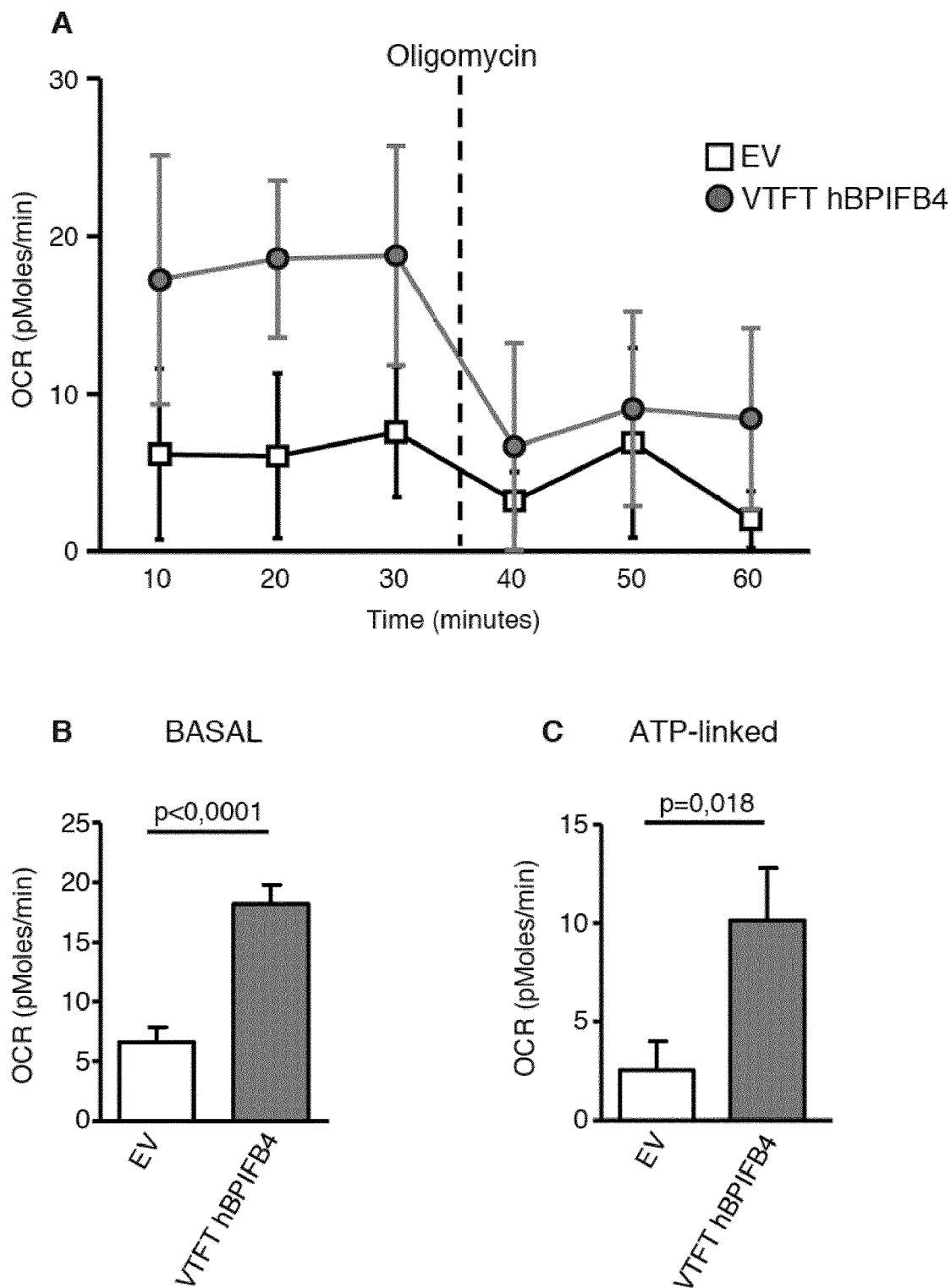
FIG. 1. Oxygen consumption rates analyses

As shown in FIG. 1, VTFT-hBPIFB4 has a greater capacity to promote and sustain OXPHOS, when compared to EV. FIG. 1B shows that VTFT-hBPIFB4 transfected cells have basal OCR levels significantly higher than EV transfected cells. FIG. 1C shows the ATP-linked rate, which is the basal rate minus the rate measured after the addition of oligomycin, a compound that blocks ATP synthesis. This value indicates that the amount of OCR dedicated for ATP production is higher in VTFT-hBPIFB4 transfected cells than in EV transfected cells. Taken together, these results showed that VTFT-hBPIFB4 induces the cells to be bioenergetically more active from untreated cells.

Accordingly, the basal ECAR (FIG. 2B) and the glycolytic capacity (FIG. 2C)—evaluated as the difference between maximal glycolysis and the treatment with glycolytic inhibitor 2DG—were statistically increased in cells transfected with VTFT-hBPIFB4 when compared to cells transfected with EV.

In conclusion, VTFT-hBPIFB4 transfected cells, having higher OCR and ECAR, are metabolically more active than control cells. VTFT-hBPIFB4 has a role in the modulation of metabolic machinery of the cell.

To confirm this data by a complementary approach, we treated human fetal fibroblasts C1-Bio 86 with hBPIFB4 and VTFT-hBPIFB4 recombinant protein variants and we measured the mitochondrial volume. As shown in FIG. 3, the average volume of mitochondria of fibroblasts treated with VTFT-hBPIFB4 is larger than the mitochondrial volume untreated fibroblasts and significantly larger than the mitochondrial volume of fibroblasts treated with hBPIFB4. In agreement with our findings, it is reported that mitochondrial volume is proportional with the bio-energetic activity of the cell.

Example 2—Huntington's Disease Model

The therapeutic potential of AAV-VTFT-hBPIFB4 was investigated in a transgenic mouse model of Huntington's disease (HD). HD is caused by expansion of the polyglutamine tract coded by poly CAG in the N-terminal region of the Huntington protein (Htt). The R6/2 mouse model is a transgenic mouse harbouring a poly CAG expansion in the exon 1 of the Htt gene, between 115 and 150 repeats. This is the most used and best characterized model for the human pathology and is characterized by a progressive loss of cognitive and motor functions, showing various degrees of similarity with the human condition, both at the molecular level, with similar toxic aggregation of mutant Htt, and at the clinical settings, with motor deficit clearly resembling the human condition.

Analysis of Motor Behaviour

Fine-motor skills and coordination were measured using well-validated motor tests as previously described. All tests took place during the light phase of the light-dark cycle. Six to nine mice per experimental group were used in each test. All mice received training for two consecutive days on each instrument and task before performing motor behaviour measurements. Before training and testing, mice underwent a period of habituation to the testing room and equipment. Motor coordination and balance were tested on a Rotarod apparatus (Ugo BasileSrl). Mice were tested at fixed speed (20 rpm) on the Rotarod for 1 min. Each mouse was tested in three consecutive trials of 1 min each, with 1 min rest between trials. The latency to fall was recorded for each trial and averaged to give the overall time spent on the Rotarod.

Skilled walking, limb placement and limb coordination were all assessed by the Horizontal Ladder Task. Mice were recorded with a video camera as they spontaneously walked along a horizontal ladder with variable and irregular spacing between rungs. In each test session, the mouse performance was evaluated using an established footfall scoring system, which allows for qualitative and quantitative evaluation of forelimb and hind limb placement on the ladder rungs.

Seven weeks old R6/2 mice with manifested HD and wild type control mice were given a single intra-arterial injection of either AAV-VTFT-hBPIFB4, AAV-INLI-hBPIFB4, or AAV-GFP.

Progression of clasping behaviour, a typical marker of abnormal involuntary movements that interfere with coordination and posture maintenance, was monitored. All tests were carried out once a week starting from the $7^{th}$ until the $11^{th}$ week of age.

Concomitant with the analysis of motor performance, animal body weight was also measured. All mice were examined daily to determine disease progression and overall well-being.

Immunohistochemistry for Mutant Htt Aggregation

Wild-type and R6/2 mice were sacrificed by cervical dislocation. Brains were removed and trimmed by removing the olfactory bulbs and spinal cord. The remaining brain was weighed, processed and embedded in paraffin wax, and 10 mm coronal sections cut on an RM 2245 microtome (Leica Microsystems). Six mice/group were used, and four coronal sections spread over the anterior-posterior extent of the brain (200-300 μm inter-section distance) were scanned. Immunostaining for mutant Htt aggregates was carried out by using EM48 antibody (1:100) (Millipore). The average area of striatal mutant Htt aggregates per section for each mouse brain was quantified with ImageJ software and reported as aggregate area ($\mu m^2$).

Results

FIG. 4A shows a mouse clasping phenotype test on a WT mouse infected with Vehicle (left panel), a R6/2 mouse infected with Vehicle (central panel), and a R6/2 mouse infected with AAV-VTFT-hBPIFB4 (right panel). This test clearly proves the ability of AAV-VTFT-hBPIFB4 to restore the normal clasping behaviour in the R6/2 mouse model.

FIGS. 4B and C show the analysis of motor deficit progression through two different tests in WT or R6/2 mice infected with AAV-GFP or AAV-VTFT-hBPIFB4. The Horizontal Ladder Task test consists in the evaluation of the ability of animal of complete a distance on a series of metal rungs. The Rotarod test measures how long animals can walk on a rotating bar with an increasing rotational speed. Both Horizontal Ladder Task and Rotarod tests demonstrated an almost complete retrieval of motor performance in R6/2 mice treated with AAV-VTFT-hBPIFB4 compared to WT mice and R6/2 mice treated with AAV-GFP or AAV-INLI-hBPIFB4.

As shown in FIG. 4D, weight loss, a prevalent and often debilitating feature of the pathology in humans, was significantly abated. R6/2 mice infected with AAV-GFP showed a slow decrease in body weight. AAV-VTFT-hBPIFB4 on the contrary maintains a body weight similar to WT mice. Surprisingly, preserved motor function was associated with a dramatic reduction in the area of mutant Htt aggregates in the striatum of treated HD mice: FIG. 4E shows the immunohistochemical analysis of striatum performed with the EM48 antibody, which recognizes N-terminal Htt fragments and is highly specific for inclusions. The visualization of the aggregates of mutant Htt allowed the measurement of their areas. The statistical analysis executed on these data demonstrates that the Htt aggregates in R6/2 mice infected with AAV-VTFT-hBPIFB4 have a reduced area in comparison to R6/2 mice infected with AAV-GFP.

Overexpression of VTFT-hBPIFB4 stops the progression of Huntington's disease and reduces mutant Htt aggregate area in R6/2 mice.

Example 3—Huntington's Disease Model: Oral Administration of VTFT-hBPIFB4 Recombinant Protein Cloning and Purification of Recombinant VTFT-hBPIFB4-His Protein The VTFT-hBPIFB4 coding sequence was PCR amplified and cloned in fusion with His-Tag in pCDH cloning and expression vector under the EF-1 promoter. HEK293T cells were transfected with the appropriate vector using the $CaCl_2$) and HBS method. Cells expressing BPIFB4-His protein were harvested after 48 h from transfection and diluted in lysis buffer/binding buffer (20 mM sodium phosphate, 300 mM NaCl, 20 mM imidazole, pH 8.0). The cell extract was digested with DNasiI (Promega) and sonicated. The recombinant protein was purified using affinity Nuvia IMAC Resin (Bio-Rad) under native conditions, washed and eluted from the column with elution buffer (20 mM sodium phosphate, 300 mM NaCl, 150-200 mM imidazole, pH 8.0). The quality and purity of BPIFB4-His recombinant protein was checked with Coomassie staining and Western blotting with anti-BPIFB4 (Abcam) and anti-His-tag (Cell Signaling) antibodies.

Analysis of Motor Behaviour

The Horizontal Ladder Task was used as described in Example 2.

Seven weeks old R6/2 mice with manifested HD and wild type control mice were orally treated with 1 μg or 3 μg VTFT-hBPIFB4 recombinant protein. The infusion of protein was performed by gavage every 3 days starting from the 7th week of the animals' age.

Progression of clasping behaviour, a typical marker of abnormal involuntary movements that interfere with coordination and posture maintenance, was monitored. All tests were carried out once a week starting from the $7^{th}$ until the $11^{th}$ week of age.

All mice were examined daily to determine disease progression and overall well-being.

Results

FIG. 5 shows the analysis of motor deficit progression through the Horizontal Ladder Task test. The performance in the test of the mice in the 3 μg dosed group did not deteriorate over the study period (between 7 and 9 weeks of age) whereas the performance in the test of the mice in the 1 μg dosed group did deteriorate. These results indicate that VTFT-hBPIFB4 is capable of having a beneficial effect when administered via the oral route.

Example 4—VTFT-hBPIFB4 Therapeutic Effect on Motor Function is Mediated by CXCR4

In order to test whether the in vivo therapeutic effect on motor function of VTFT-hBPIFB4 is mediated by CXCR4, R6/2 Huntington's disease mouse model and motor behaviour tests were utilized as in Example 2. There were four groups of mice, one group injected intra-arterial with AAV-GFP alone (N=3), one group injected intra-arterial with AAV-GFP with AMD3100 (N=3), a CXCR4 inhibitor, one group injected intra-arterial with AAV-VTFT-hBPIFB4 alone (N=4) and one group injected intra-arterial with AAV-VTFT-hBPIFB4 with AMD3100 (N=4). AMD3100 was administered every day intra-peritoneal after AAV injection.

Results

The inventors found that administration of AAV-VTFT-hBPIFB4 to R6/2 mice stops the progression of Huntington's disease and reduces mutant Htt aggregate area. FIGS. 6A and B show that when R6/2 mice have been infected with VTFT-hBPIFB4 the motor deficit progression is impeded, but this beneficial effect is blunted if the VTFT-hBPIFB4 infected R6/2 mice are treated with AMD3100, a CXCR4 inhibitor.

Both the Horizontal Ladder Task and Rotarod tests demonstrated that the retrieval of motor performance in R6/2 mice infected with AAV-VTFT-hBPIFB4 did not occur in VTFT-hBPIFB4 infected R6/2 mice treated with AMD3100. They had experimental values similar to the controls (AAV-GFP injected mice or AAV-GFP+AMD3100 treated mice).

FIG. 6C shows that weight loss, a feature of the pathology in humans, was less pronounced in R6/2 mice infected with AAV-VTFT-hBPIFB4 compared with mice treated with AAV-VTFT-hBPIFB4+AMD3100 or in controls.

Example 5—Evaluation of VTFT-hBPIFB4 Effect on Generation of Monocyte-Derived Dendritic Cells DCs are a plastic lineage able to process and integrate signals from the microenvironment. Under pro-inflammatory conditions stimulatory DCs promote an effective immune response by stimulating T cell proliferation and shaping T cell responses toward TH 1, TH 2, or TH17 phenotypes. This crucial role allows the immune system to clear pathogens and aberrant proteins and keep transformed cells in check (Schmidt et al. (2012)).

It has been reported that human monocyte derived-dendritic cells (DCs) express CXCR4. Its engagement enhances DC maturation and survival to initiate an effective acquired immune response (Delgado Martin et al. (2011), Kabashima et al. (2007)).

Generation of Monocyte-Derived Dendritic Cells (MDDC) and Cytofluorimetric Analysis Peripheral blood mononuclear cells from healthy donors were isolated over Ficoll-Hypaque gradients (lymphocyte separation medium; MP Biomedicals, Aurora, OH, USA). To generate immature dendritic cells (iDCs), CD14+ monocytes were positively selected from PBMC by immunomagnetic procedure (Miltenyi Biotec, Calderara di Reno, Italy). Immature MDDC were then obtained by culturing CD14+ cells at 106 cells/ml in RPMI 1640 (Invitrogen), 10% FCS (Fetal Calf Serum), 50 ng/ml GM-CSF and 1000 U/ml IL-4 in the presence or absence of 18 ng/ml of INLI-hBPIFB4 or alternatively 18 ng/ml of VTFT-hBPIFB4. FACS analysis of these After 6-8 d of culture, iDCs were extensively washed to remove INLI-hBPIFB4 or VTFT-BPIFB4, and terminally differentiated by incubation with LPS at 1 ug/ml (Sigma-Aldrich, St. Louis, MO, USA) for 24 h. All cell culture was conducted at 37° C. in humidified 5% CO2 atmosphere. FACS analysis of the cells was performed to determine the percentage of CD86+ and CXCR4+ mature DCs in each group.

Flow Cytometry

Conjugated monoclonal antibodies against CD14, CD1a, CD86, CXCR4 were purchased from BD Biosciences (San Diego, CA, USA). Cells were collected and stained with the indicated antibodies for 20 min at 4° C. Data were collected and analyzed using a FACSVerse flow cytometer (Becton Dickinson, USA).

Results

Results are shown in FIG. 9 and partially summarised below.

| | CD86+ mature DC | CXCR4+ mature DC |
|---|---|---|
| Vehicle | 75.12% | 21.93% |
| hBPIFB4 (18 ng/mL) | 85.82% | 33.2% |
| VTFT-hBPIFB4 (18 ng/mL) | 88.2% | 48.3% |

DISCUSSION

LPS-matured DCs generated in the presence of recombinant VTFT-hBPIFB4 display an increased percentage of cells positive for CXCR4 expression on their surface. Accordingly, the co-stimulatory molecule CD86 is also up-regulated. These findings suggest that VTFT-hBPIFB4 enhances DC maturation and survival to initiate an acquired immune response. The differentiation of progenitor cells to DCs is dependent on mitochondrial activity (Zaccagnino et al. (2012)). Once differentiated, DCs may regulate immune responses in the CNS (Clarkson et al. (2012)). So, as for other cells, DCs are modified by VTFT-hBPIFB4 at the CXCR4 level, showing an activation status that may be expected to correspond with mitochondrial activation and a neuroprotective immune phenotype.

REFERENCES

E. Beletkaia. et al., Biochimica et Biophysica Acta 1863 (2016) 607-616

Boldogh. I. R., Pon. L. A. Biochim Biophys Acta. (2006) 1763(5-6):450-62

P. Bubber, et al., Ann. Neurol. 57 (2005) 695-703

Cagalinec M. et al., PLoSBiol. (2016) Jul. 19; 14(7)

C. M. Chen, et al., Biochem. Biophys. Res. Commun. 359 (2007) 335-340

L. Devi, et al., J. Biol. Chem. 283 (2008) 9089-9100

Ferro A., et al., Journal of Visualized Experiments, (2017) Issue 119, 22

A. L. Fink, Folding & Design February 1998, 3:R9-R23

Gao et al, J. Virol, (2004) 78: 6381-6388

Grenier. C. et al., J Neurochem. 2006 June; 97(5):1456-66

M. K. Jaiswal, B. U. Keller, Mol. Pharmacol. 75 (2009) 478-489

Koeppen, A. H. Cerebellum (2005) 4: 62

D. Lim, et al., J. Biol. Chem. 283 (2008) 5780-5789

J-M. Liu. et al., Scientific Reports 7, (2017) Article number: 64

M. Manczak, et al., Hum. Mol. Genet. 15 (2006) 1437-1449

Mori, et al., Virology, (2004) 330(2): 375-383

A. L. Orr, et al., J. Neurosci. 28 (2008) 2783-2792

Pagano, Castello, Adv Exp Med Biol. (2012) 724:291-9

Santos R., et al., Antioxidants & Redox Signaling. (2010) 13(5):651-690

Scaglia F, Northrop J L. CNS Drugs. (2006); 20(6):443-64

P. G. Sullivan, et al., J. Alzheimers Dis. 16 (2009) 741-761

Takeuchi, H., et al., Neurosci Lett (2007) 426, 69-74

Tysseling, V. M., et al., J Neuroinflammation (2011) 8, 16

J. Valla, et al., Mitochondrion 6 (2006) 323-330

Villa et al., Circ. Res. (2015) 31; 117(4):333-45

Schmidt S. V., et al., Front. Immunol. (2012); 4:3, 274

Delgado-Martin C., et al, J. Biol. Chem. (2011), 286:43, 37222-37236

Kabashima K., et al., Biochem. Biophys. Res. Commun. (2007), 361:4, 1012-1016

Zaccagnino et al., Int. J. Biochem. Cell Biol. (2012), 44:11, 1962-1969

Clarkson et al., Adv. Exp. Med. Biol (2012), 946, 309-333

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A method of reducing protein aggregation in Huntington's disease, which comprises administering to a subject in need thereof an effective amount of a polynucleotide encoding a protein which is a VTFT isoform of a BPIFB4 protein, said VTFT isoform comprising a Valine at a position corresponding to position 229 of the amino acid sequence of SEQ ID NO: 1, a Threonine at a position corresponding to position 281 of the amino acid sequence of SEQ ID NO: 1, a Phenylalanine at a position corresponding to position 488 of the amino acid sequence of SEQ ID NO: 1 and a Threonine at a position corresponding to position 494 of the amino acid sequence of SEQ ID NO: 1, and wherein the polynucleotide comprises a sequence encoding the protein of SEQ ID NO:1.

2. The method according to claim 1, wherein the polynucleotide comprises a sequence having 100% sequence identity to the nucleic acid sequence of SEQ ID NO: 2.

3. A method of reducing protein aggregation in Huntington's disease, which comprises administering to a subject in need thereof an effective amount of a vector comprising a polynucleotide encoding a protein which is a VTFT isoform of a BPIFB4 protein, said VTFT isoform comprising a Valine at a position corresponding to position 229 of the amino acid sequence of SEQ ID NO: 1, a Threonine at a position corresponding to position 281 of the amino acid sequence of SEQ ID NO: 1, a Phenylalanine at a position corresponding to position 488 of the amino acid sequence of SEQ ID NO: 1 and a Threonine at a position corresponding to position 494 of the amino acid sequence of SEQ ID NO: 1, and wherein the polynucleotide comprises a sequence encoding the protein of SEQ ID NO:1.

4. The method according to claim 3, wherein the polynucleotide comprises a sequence having 100% sequence identity to the nucleic acid sequence of SEQ ID NO: 2.

5. The method according to claim 3, wherein the vector is selected from adeno-associated viral vectors, adenovirus vectors, herpes virus vectors, parvovirus vectors, and lentivirus vectors.

6. The method according to claim 5, wherein the vector is an adeno-associated viral vector selected from AAV1, AAV2, AAV3, AAV4, AAV5, AAV6, AAV7, AAV8 and AAV9.

7. The method according to claim 5, wherein the vector is an adeno-associated viral vector.

8. The method according to claim 6, wherein the adeno-associated viral vector is AAV9.

* * * * *